(12) United States Patent
Zucherman et al.

(10) Patent No.: US 7,931,674 B2
(45) Date of Patent: Apr. 26, 2011

(54) INTERSPINOUS PROCESS IMPLANT HAVING DEPLOYABLE WING AND METHOD OF IMPLANTATION

(75) Inventors: James F. Zucherman, San Francisco, CA (US); Ken Y. Hsu, San Francisco, CA (US); Charles J. Winslow, Walnut Creek, CA (US); John J. Flynn, West Milford, NJ (US); Steve Mitchell, Pleasant Hill, CA (US); Scott A. Yerby, Montara, CA (US); John A. Markwart, Castro Valley, CA (US)

(73) Assignee: Kyphon SARL, Neuchatel (CH)

( * ) Notice: Subject to any disclaimer, the term of this patent is extended or adjusted under 35 U.S.C. 154(b) by 955 days.

(21) Appl. No.: 11/377,971

(22) Filed: Mar. 17, 2006

(65) Prior Publication Data
US 2006/0264938 A1    Nov. 23, 2006

Related U.S. Application Data

(60) Provisional application No. 60/663,885, filed on Mar. 21, 2005.

(51) Int. Cl.
*A61B 17/70* (2006.01)
(52) U.S. Cl. ........................ 606/249; 606/248
(58) Field of Classification Search .................. 606/60, 606/246–279, 63, 310, 323, 327; 623/17.11–17.16; 411/24, 25, 32, 340
See application file for complete search history.

(56) References Cited

U.S. PATENT DOCUMENTS

| | | | | |
|---|---|---|---|---|
| 624,969 | A | * | 5/1899 | Peterson ........................ 411/340 |
| 1,153,797 | A | * | 9/1915 | Kegreisz ......................... 411/24 |
| 1,516,347 | A | | 11/1924 | Pataky |
| 1,870,942 | A | | 8/1932 | Beatty |
| 2,077,804 | A | * | 4/1937 | Morrison ........................ 606/68 |
| 2,299,308 | A | | 10/1942 | Creighton |

(Continued)

FOREIGN PATENT DOCUMENTS

CA          2015507         1/1991

(Continued)

OTHER PUBLICATIONS

Minns, R.J., et al., "Preliminary Design and Experimental Studies of a Novel Soft Implant for Correcting Sagittal Plane Instability in the Lumbar Spine," SPINE, vol. 22, No. 16, pp. 1819-1825, Lippincott-Raven Publishers (1997).

(Continued)

*Primary Examiner* — Thomas C Barrett
*Assistant Examiner* — Christine L Nelson
(74) *Attorney, Agent, or Firm* — Coats and Bennett, P.L.L.C.

(57) ABSTRACT

Systems and method in accordance with an embodiment of the present invention can includes an implant comprising a first wing, a spacer extending from the first wing, and a distraction guide. The distraction guide is arranged in a first configuration to pierce and/or distract tissue associated with adjacent spinous processes extending from vertebrae of a targeted motion segment. The implant can be positioned between the adjacent spinous processes and once positioned, the distraction guide can be arranged in a second configuration. When arranged in a second configuration, the distraction guide can act as a second wing. The first wing and the second wing can limit or block movement of the implant along a longitudinal axis of the implant.

9 Claims, 31 Drawing Sheets

U.S. PATENT DOCUMENTS

| | | | |
|---|---|---|---|
| 2,456,806 A | 12/1948 | Wolffe | 33/174 |
| 2,485,531 A * | 10/1949 | Dzus et al. | 606/310 |
| 2,607,370 A * | 8/1952 | Anderson | 138/90 |
| 2,677,369 A | 5/1954 | Knowles | 128/92 |
| 2,685,877 A * | 8/1954 | Dobelle | 623/23.11 |
| 3,065,659 A * | 11/1962 | Eriksson et al. | 411/25 |
| 3,108,595 A | 10/1963 | Overment | |
| 3,426,364 A | 2/1969 | Lumb | 3/1 |
| 3,643,658 A | 2/1972 | Steinemenan | 128/920 |
| 3,648,691 A | 3/1972 | Lumb | 128/920 |
| 3,779,239 A | 12/1973 | Fischer et al. | |
| 3,867,728 A | 2/1975 | Stubstad | 3/1 |
| 3,875,595 A | 4/1975 | Froning | 3/1 |
| 4,011,602 A | 3/1977 | Rybicki et al. | |
| 4,034,418 A | 7/1977 | Jackson | 3/1.911 |
| 4,219,015 A | 8/1980 | Steineman | 128/92 D |
| 4,237,875 A | 12/1980 | Termanini | |
| 4,257,409 A | 3/1981 | Bacal et al. | |
| 4,274,324 A * | 6/1981 | Giannuzzi | 411/38 |
| 4,289,123 A | 9/1981 | Dunn | |
| 4,309,777 A | 1/1982 | Patil | 3/1.91 |
| 4,349,921 A | 9/1982 | Kuntz | 3/1 |
| 4,369,769 A | 1/1983 | Edwards | 128/69 |
| 4,401,112 A | 8/1983 | Rezaian | 128/92 B |
| 4,455,690 A | 6/1984 | Homsy | 3/1 |
| 4,479,491 A | 10/1984 | Martin | 128/92 B |
| 4,499,636 A * | 2/1985 | Tanaka | 24/289 |
| 4,501,269 A | 2/1985 | Bagby | 128/96 G |
| 4,502,161 A | 3/1985 | Wall | 623/18 |
| 4,519,100 A * | 5/1985 | Wills et al. | 606/63 |
| 4,553,273 A | 11/1985 | Wu | 623/18 |
| 4,554,914 A | 11/1985 | Kapp | 128/92 C |
| 4,573,454 A | 3/1986 | Hoffman | |
| 4,592,341 A | 6/1986 | Omagari et al. | |
| 4,599,084 A | 7/1986 | Nashef | 623/16 |
| 4,599,086 A | 7/1986 | Doty | 623/17 |
| 4,604,995 A | 8/1986 | Stephens | 128/69 |
| 4,611,582 A | 9/1986 | Duff | 128/69 |
| 4,632,101 A | 12/1986 | Freedland | |
| 4,636,217 A | 1/1987 | Ogilvie | 623/17 |
| 4,643,178 A | 2/1987 | Nastari | 128/92 |
| 4,646,998 A * | 3/1987 | Pate | 248/250 |
| 4,657,550 A | 4/1987 | Daher | 623/17 |
| 4,662,808 A * | 5/1987 | Camilleri | 411/340 |
| 4,685,447 A | 8/1987 | Iversen | 128/1 R |
| 4,686,970 A | 8/1987 | Dove et al. | |
| 4,696,290 A | 9/1987 | Steffee | 128/69 |
| 4,704,057 A * | 11/1987 | McSherry | 411/55 |
| 4,714,469 A | 12/1987 | Kenna | 623/17 |
| 4,743,256 A | 5/1988 | Brantigan | 623/17 |
| 4,759,670 A * | 7/1988 | Linder et al. | 411/43 |
| 4,759,769 A | 7/1988 | Hedman et al. | |
| 4,772,287 A | 9/1988 | Ray | 623/17 |
| 4,787,378 A * | 11/1988 | Sodhi | 606/67 |
| 4,790,303 A | 12/1988 | Steffee | 128/924 M |
| 4,822,226 A * | 4/1989 | Kennedy | 411/342 |
| 4,827,918 A | 5/1989 | Olerud | |
| 4,834,600 A * | 5/1989 | Lemke | 411/55 |
| 4,834,757 A | 5/1989 | Brantigan | 623/17 |
| 4,863,476 A | 9/1989 | Shepperd | |
| 4,878,915 A | 11/1989 | Brantigan | 623/17 |
| 4,886,405 A | 12/1989 | Blomberg | |
| 4,892,545 A | 1/1990 | Day et al. | |
| 4,904,260 A | 2/1990 | Ray | 623/17 |
| 4,904,261 A | 2/1990 | Dove | 623/17 |
| 4,913,134 A | 4/1990 | Luque | 128/69 |
| 4,913,144 A | 4/1990 | Del Medico | |
| 4,923,471 A | 5/1990 | Morgan | 623/16 |
| 4,931,055 A | 6/1990 | Bumpus et al. | |
| 4,932,975 A | 6/1990 | Main | 623/17 |
| 4,936,848 A | 6/1990 | Bagby | 623/17 |
| 4,946,378 A | 8/1990 | Hirayama | 623/17 |
| 4,961,740 A | 10/1990 | Ray | 606/61 |
| 4,969,887 A | 11/1990 | Sodhi | |
| 4,969,888 A | 11/1990 | Scholten | 606/94 |
| 5,000,166 A | 3/1991 | Karpf | |
| 5,011,484 A | 4/1991 | Breard | 606/61 |
| 5,015,247 A | 5/1991 | Michelson | 606/61 |
| 5,015,255 A | 5/1991 | Kuslich | 623/17 |
| 5,026,373 A | 6/1991 | Ray | 606/61 |
| 5,035,716 A | 7/1991 | Downey | 623/17 |
| 5,047,055 A | 9/1991 | Bao | 623/17 |
| 5,055,104 A | 10/1991 | Ray | 606/61 |
| 5,059,193 A | 10/1991 | Kuslich | 606/61 |
| 5,059,194 A | 10/1991 | Michelson | 606/61 |
| 5,062,845 A | 11/1991 | Kuslich | 606/80 |
| 5,062,850 A | 11/1991 | MacMillan | 623/17 |
| 5,074,864 A | 12/1991 | Cozad | 606/54 |
| 5,084,049 A | 1/1992 | Asher et al. | 606/61 |
| 5,088,869 A | 2/1992 | Greenslade | 411/386 |
| 5,092,866 A | 3/1992 | Breard | 606/61 |
| 5,098,433 A * | 3/1992 | Freedland | 606/63 |
| 5,105,255 A | 4/1992 | Shannon | 357/68 |
| 5,122,130 A | 6/1992 | Keller | 606/61 |
| 5,123,926 A | 6/1992 | Pisharodi | 623/17 |
| 5,127,912 A | 7/1992 | Ray | 606/61 |
| 5,147,404 A | 9/1992 | Downey | 623/17 |
| 5,167,662 A | 12/1992 | Hayes | 606/61 |
| 5,167,665 A | 12/1992 | McKinney | 606/75 |
| 5,171,278 A | 12/1992 | Pisharodi | |
| 5,180,381 A | 1/1993 | Aust | 606/61 |
| 5,192,327 A | 3/1993 | Brantigan | 623/17 |
| 5,201,734 A | 4/1993 | Cozad et al. | |
| 5,258,031 A | 11/1993 | Salib | 623/17 |
| 5,263,953 A | 11/1993 | Bagby | 606/61 |
| 5,267,999 A | 12/1993 | Olerud | |
| 5,275,601 A | 1/1994 | Gogolewski | 606/72 |
| 5,290,312 A | 3/1994 | Kojimoto | 623/17 |
| 5,300,073 A | 4/1994 | Ray | 606/61 |
| 5,304,178 A | 4/1994 | Stahurski | 606/61 |
| 5,306,275 A | 4/1994 | Bryan | 606/61 |
| 5,306,309 A | 4/1994 | Wagner | 623/17 |
| 5,306,310 A | 4/1994 | Siebels | |
| 5,312,405 A | 5/1994 | Korotko et al. | |
| 5,352,225 A | 10/1994 | Yuan | 606/61 |
| 5,360,430 A | 11/1994 | Lin | |
| 5,366,455 A | 11/1994 | Dove | 606/61 |
| 5,370,697 A | 12/1994 | Baumgartner | |
| 5,387,213 A | 2/1995 | Breard | 606/61 |
| 5,390,683 A | 2/1995 | Pisharodi | 128/898 |
| 5,391,168 A | 2/1995 | Sanders | 606/61 |
| 5,395,370 A | 3/1995 | Muller et al. | |
| 5,395,372 A | 3/1995 | Holt | 606/61 |
| 5,401,269 A | 3/1995 | Buttner-Janz et al. | |
| 5,403,316 A | 4/1995 | Ashman | |
| 5,415,661 A | 5/1995 | Holmes | 606/69 |
| 5,437,672 A | 8/1995 | Alleyne | 606/61 |
| 5,437,674 A | 8/1995 | Worcel et al. | |
| 5,439,463 A | 8/1995 | Lin | |
| 5,443,514 A | 8/1995 | Steffee | 623/17 |
| 5,454,812 A | 10/1995 | Lin | 606/61 |
| 5,456,722 A | 10/1995 | McLeod | 623/13 |
| 5,458,638 A | 10/1995 | Kuslich | 623/17 |
| 5,458,641 A | 10/1995 | Ramirez Jimenez | 623/17 |
| 5,458,643 A | 10/1995 | Oka | 623/18 |
| 5,468,242 A | 11/1995 | Reisberg | 606/69 |
| 5,470,333 A | 11/1995 | Ray | 606/61 |
| 5,480,442 A | 1/1996 | Bertagnoli | |
| 5,491,882 A | 2/1996 | Walston | 29/419.1 |
| 5,496,318 A | 3/1996 | Howland | 606/61 |
| 5,505,732 A | 4/1996 | Michelson | 606/61 |
| 5,507,745 A | 4/1996 | Logroscino | 606/61 |
| 5,507,823 A | 4/1996 | Walston | 623/21 |
| 5,514,180 A | 5/1996 | Heggeness | 623/17 |
| 5,518,498 A | 5/1996 | Lindenberg et al. | |
| 5,527,312 A | 6/1996 | Ray | 606/61 |
| 5,531,747 A | 7/1996 | Ray | 606/61 |
| 5,534,028 A | 7/1996 | Bao | 623/17 |
| 5,534,029 A | 7/1996 | Shima | 623/17 |
| 5,540,689 A | 7/1996 | Sanders | 606/61 |
| 5,549,679 A | 8/1996 | Kuslich | 623/17 |
| 5,554,191 A | 9/1996 | Lahille | 623/17 |
| 5,562,662 A | 10/1996 | Brumfield et al. | |
| 5,562,735 A | 10/1996 | Margulies | |
| 5,562,736 A | 10/1996 | Ray | 623/17 |
| 5,571,191 A | 11/1996 | Fitz | 623/17 |
| 5,571,192 A | 11/1996 | Schonhoffer | |

| | | | | | | | |
|---|---|---|---|---|---|---|---|
| 5,577,995 | A | 11/1996 | Walker ............................ 601/120 | 6,152,926 | A | 11/2000 | Zucherman .................... 606/61 |
| 5,584,832 | A | 12/1996 | Schlapfer ......................... 606/69 | 6,152,927 | A | 11/2000 | Farris ............................. 606/69 |
| 5,593,409 | A | 1/1997 | Michelson ........................ 606/61 | 6,156,038 | A | 12/2000 | Zucherman .................... 606/61 |
| 5,601,553 | A | 2/1997 | Trebing ............................ 606/61 | 6,156,067 | A | 12/2000 | Bryan ......................... 623/17.15 |
| 5,603,713 | A | 2/1997 | Aust ................................. 606/61 | 6,183,471 | B1 | 2/2001 | Zucherman .................... 606/61 |
| 5,609,634 | A | 3/1997 | Voydeville ....................... 623/17 | 6,190,387 | B1 | 2/2001 | Zucherman .................... 606/61 |
| 5,609,635 | A | 3/1997 | Michelson | 6,190,413 | B1 | 2/2001 | Sutcliffe |
| 5,616,142 | A | 4/1997 | Yuan ................................ 606/61 | 6,190,414 | B1 | 2/2001 | Young ......................... 623/17.15 |
| 5,623,984 | A | 4/1997 | Nozaki ............................. 164/457 | 6,193,721 | B1 | 2/2001 | Michelson .................... 606/70 |
| 5,628,756 | A | 5/1997 | Barker, Jr. ....................... 606/139 | 6,200,322 | B1 | 3/2001 | Branch ............................. 606/96 |
| 5,630,816 | A | 5/1997 | Kambin | 6,206,922 | B1 | 3/2001 | Zdeblick .................... 623/17.11 |
| 5,645,597 | A | 7/1997 | Krapiva ............................ 623/17 | 6,214,050 | B1 | 4/2001 | Huene |
| 5,645,599 | A | 7/1997 | Samani ............................ 623/17 | 6,217,580 | B1 | 4/2001 | Levin .............................. 606/71 |
| 5,653,761 | A | 8/1997 | Pisharodi ......................... 623/17 | 6,224,602 | B1 | 5/2001 | Hayes ............................. 606/69 |
| 5,653,762 | A | 8/1997 | Pisharodi | 6,224,607 | B1 | 5/2001 | Michelson .................... 606/96 |
| 5,653,763 | A | 8/1997 | Errico et al. | 6,228,900 | B1 | 5/2001 | Shen .............................. 522/153 |
| 5,658,286 | A | 8/1997 | Sava ................................. 606/61 | 6,234,705 | B1 | 5/2001 | Troxell .......................... 403/237 |
| 5,658,335 | A | 8/1997 | Allen | 6,235,030 | B1 * | 5/2001 | Zucherman et al. ........ 606/249 |
| 5,665,122 | A | 9/1997 | Kambin | 6,238,397 | B1 | 5/2001 | Zucherman .................... 606/61 |
| 5,672,177 | A | 9/1997 | Seldin ............................. 606/71 | 6,261,296 | B1 | 7/2001 | Aebi ............................... 606/90 |
| 5,674,295 | A | 10/1997 | Ray ................................. 623/17 | 6,280,444 | B1 | 8/2001 | Zucherman .................... 606/61 |
| 5,674,296 | A | 10/1997 | Bryan ............................... 623/17 | 6,293,949 | B1 | 9/2001 | Justis ............................. 606/61 |
| 5,676,702 | A | 10/1997 | Ratron ............................. 623/17 | 6,306,136 | B1 | 10/2001 | Baccelli ......................... 606/61 |
| 5,685,826 | A | 11/1997 | Bonutti | 6,332,882 | B1 | 12/2001 | Zucherman .................... 606/61 |
| 5,690,649 | A | 11/1997 | Li | 6,332,883 | B1 | 12/2001 | Zucherman .................... 606/61 |
| 5,693,100 | A | 12/1997 | Pisharodi | 6,336,930 | B1 | 1/2002 | Stalcup et al. |
| 5,702,395 | A | 12/1997 | Hopf | 6,348,053 | B1 | 2/2002 | Cachia |
| 5,702,452 | A | 12/1997 | Argenson et al. | 6,352,537 | B1 | 3/2002 | Strnad ............................ 606/61 |
| 5,702,455 | A | 12/1997 | Saggar ............................. 623/17 | 6,364,883 | B1 | 4/2002 | Santilli |
| 5,707,390 | A | 1/1998 | Bonutti | 6,368,351 | B1 | 4/2002 | Glenn ......................... 623/17.15 |
| 5,716,416 | A | 2/1998 | Lin | 6,371,984 | B1 | 4/2002 | Van Dyke .................... 623/11.11 |
| 5,723,013 | A | 3/1998 | Jeanson et al. | 6,371,987 | B1 | 4/2002 | Weiland et al. |
| 5,725,341 | A | 3/1998 | Hofmeister | 6,375,682 | B1 | 4/2002 | Fleischmann et al. |
| 5,725,582 | A | 3/1998 | Bevan ............................. 623/17 | 6,379,355 | B1 | 4/2002 | Zucherman .................... 606/61 |
| 5,741,261 | A | 4/1998 | Moskovitz ..................... 606/79 | 6,383,186 | B1 | 5/2002 | Michelson .................... 606/69 |
| 5,746,762 | A | 5/1998 | Bass | 6,395,030 | B1 | 5/2002 | Songer ....................... 623/17.11 |
| 5,755,797 | A | 5/1998 | Baumgartner | 6,398,783 | B1 | 6/2002 | Michelson .................... 606/70 |
| 5,766,251 | A | 6/1998 | Koshino .......................... 623/16 | 6,402,750 | B1 | 6/2002 | Atkinson et al. |
| 5,766,252 | A | 6/1998 | Henry ............................. 623/17 | 6,402,751 | B1 | 6/2002 | Hoeck et al. |
| 5,800,438 | A | 9/1998 | Tuke ................................ 606/90 | 6,402,756 | B1 | 6/2002 | Ralph ............................. 606/71 |
| 5,800,547 | A | 9/1998 | Schafer et al. | 6,416,776 | B1 | 7/2002 | Shamie .......................... 424/423 |
| 5,810,815 | A | 9/1998 | Morales | 6,419,676 | B1 | 7/2002 | Zucherman .................... 606/61 |
| 5,824,098 | A | 10/1998 | Stein ................................ 623/20 | 6,419,677 | B2 | 7/2002 | Zucherman .................... 606/61 |
| 5,836,948 | A | 11/1998 | Zucherman .................... 606/61 | 6,419,703 | B1 | 7/2002 | Fallin ........................ 623/17.11 |
| 5,849,004 | A | 12/1998 | Bramlet | 6,419,704 | B1 | 7/2002 | Ferree |
| 5,860,977 | A | 1/1999 | Zucherman .................... 606/61 | 6,428,542 | B1 | 8/2002 | Michelson .................... 606/70 |
| 5,865,846 | A | 2/1999 | Bryan ............................. 623/17 | 6,436,145 | B1 | 8/2002 | Miller ....................... 623/20.34 |
| 5,876,402 | A | 3/1999 | Errico ............................. 606/61 | 6,440,169 | B1 | 8/2002 | Elberg et al. ............... 623/17.16 |
| 5,876,404 | A | 3/1999 | Zucherman .................... 606/61 | 6,447,513 | B1 | 9/2002 | Griggs |
| 5,879,396 | A | 3/1999 | Walston .......................... 623/21 | 6,451,019 | B1 | 9/2002 | Zucherman .................... 606/61 |
| 5,885,299 | A | 3/1999 | Winslow ........................ 606/99 | 6,451,020 | B1 | 9/2002 | Zucherman .................... 606/61 |
| 5,888,196 | A | 3/1999 | Bonutti | 6,454,771 | B1 | 9/2002 | Michelson .................... 606/70 |
| 5,888,224 | A | 3/1999 | Beckers .......................... 627/17 | 6,458,131 | B1 | 10/2002 | Ray ................................ 606/61 |
| 5,888,226 | A | 3/1999 | Rogozinski .................... 623/17 | 6,478,796 | B2 | 11/2002 | Zucherman .................... 606/61 |
| 5,941,881 | A | 8/1999 | Barnes | 6,500,178 | B2 | 12/2002 | Zucherman .................... 606/61 |
| 5,951,555 | A | 9/1999 | Rehak ............................. 606/61 | 6,514,256 | B2 | 2/2003 | Zucherman .................... 606/61 |
| 5,976,186 | A | 11/1999 | Bao ................................. 623/17 | 6,520,991 | B2 | 2/2003 | Huene |
| 5,980,523 | A | 11/1999 | Jackson | 6,527,776 | B1 | 3/2003 | Michelson .................... 606/70 |
| 6,001,130 | A | 12/1999 | Bryan ............................. 623/17 | 6,554,833 | B2 | 4/2003 | Levy |
| 6,022,376 | A | 2/2000 | Assell ............................. 623/17 | 6,558,423 | B1 | 5/2003 | Michelson .................... 623/17.11 |
| 6,030,162 | A | 2/2000 | Huebner ........................ 411/413 | 6,558,686 | B1 | 5/2003 | Darouiche .................... 424/423 |
| 6,045,552 | A | 4/2000 | Zucherman .................... 606/69 | 6,565,570 | B2 | 5/2003 | Sterett ............................ 606/69 |
| 6,045,554 | A | 4/2000 | Grooms .......................... 606/73 | 6,565,605 | B2 | 5/2003 | Goble ........................ 623/17.11 |
| 6,048,204 | A | 4/2000 | Klardie .......................... 433/174 | 6,579,318 | B2 | 6/2003 | Varga ......................... 623/17.11 |
| 6,048,342 | A | 4/2000 | Zucherman .................... 606/61 | 6,579,319 | B2 | 6/2003 | Goble ........................ 623/17.11 |
| 6,048,344 | A | 4/2000 | Schenk ........................... 606/73 | 6,582,433 | B2 | 6/2003 | Yun ................................ 606/61 |
| 6,068,630 | A | 5/2000 | Zucherman .................... 606/61 | 6,582,467 | B1 | 6/2003 | Teitelbaum et al. |
| RE36,758 | E | 6/2000 | Fitz ................................ 623/17 | 6,592,585 | B2 | 7/2003 | Lee et al. |
| 6,074,390 | A | 6/2000 | Zucherman .................... 606/61 | 6,592,586 | B1 | 7/2003 | Michelson .................... 606/71 |
| 6,090,112 | A | 7/2000 | Zucherman .................... 606/61 | 6,610,091 | B1 | 8/2003 | Reiley ........................ 623/17.11 |
| 6,099,531 | A | 8/2000 | Bonutti .......................... 606/87 | 6,620,163 | B1 | 9/2003 | Michelson .................... 606/61 |
| 6,113,639 | A | 9/2000 | Ray ............................. 623/17.16 | 6,626,944 | B1 | 9/2003 | Taylor ........................ 623/17.16 |
| 6,126,689 | A | 10/2000 | Brett | 6,641,585 | B2 | 11/2003 | Sato et al. ...................... 606/61 |
| 6,126,691 | A | 10/2000 | Kasra et al. | 6,645,207 | B2 | 11/2003 | Dixon et al. |
| 6,127,597 | A | 10/2000 | Beyar et al. | 6,652,527 | B2 | 11/2003 | Zucherman .................... 606/61 |
| 6,129,730 | A | 10/2000 | Bono ............................. 606/73 | 6,652,534 | B2 | 11/2003 | Zucherman .................. 606/102 |
| 6,132,464 | A | 10/2000 | Martin ............................ 623/17 | 6,669,729 | B2 | 12/2003 | Chin ........................... 623/17.11 |
| 6,139,550 | A | 10/2000 | Michelson .................... 606/69 | 6,685,742 | B1 | 2/2004 | Jackson |
| 6,149,652 | A | 11/2000 | Zucherman .................... 606/61 | 6,695,842 | B2 | 2/2004 | Zucherman .................... 606/61 |

| | | |
|---|---|---|
| 6,699,246 B2 | 3/2004 | Zucherman .................... 606/61 |
| 6,699,247 B2 | 3/2004 | Zucherman .................... 606/61 |
| 6,709,435 B2 | 3/2004 | Lin |
| 6,712,819 B2 | 3/2004 | Zucherman .................... 606/61 |
| 6,712,852 B1 | 3/2004 | Chung ...................... 623/17.11 |
| 6,723,126 B1 | 4/2004 | Berry |
| 6,730,126 B2 | 5/2004 | Boehm, Jr. et al. |
| 6,730,127 B2 | 5/2004 | Michelson ................. 623/17.16 |
| 6,733,534 B2 | 5/2004 | Sherman |
| 6,736,818 B2 | 5/2004 | Perren et al. |
| 6,743,257 B2 | 6/2004 | Castro |
| 6,746,485 B1 | 6/2004 | Zucherman ............... 623/17.16 |
| 6,752,831 B2 | 6/2004 | Sybert ....................... 623/13.17 |
| 6,758,863 B2 | 7/2004 | Estes et al. |
| 6,761,720 B1 | 7/2004 | Senegas .......................... 606/61 |
| 6,764,491 B2 | 7/2004 | Frey et al. ...................... 606/85 |
| 6,770,096 B2 | 8/2004 | Bolger et al. |
| 6,783,527 B2 | 8/2004 | Drewry .......................... 606/61 |
| 6,783,530 B1 | 8/2004 | Levy |
| 6,796,983 B1 | 9/2004 | Zucherman .................... 606/61 |
| 6,800,670 B2 | 10/2004 | Shen ............................... 522/153 |
| 6,811,567 B2 | 11/2004 | Reiley ...................... 623/17.11 |
| 6,835,205 B2 | 12/2004 | Atkinson et al. |
| 6,902,566 B2 | 6/2005 | Zucherman .................... 606/61 |
| 6,905,512 B2 | 6/2005 | Paes et al. |
| 6,926,728 B2 | 8/2005 | Zucherman et al. ......... 606/190 |
| 6,936,050 B2 | 8/2005 | Michelson ...................... 606/61 |
| 6,936,051 B2 | 8/2005 | Michelson ...................... 606/61 |
| 6,946,000 B2 | 9/2005 | Senegas et al. |
| 6,949,123 B2 | 9/2005 | Reiley ....................... 623/17.11 |
| 6,969,390 B2 | 11/2005 | Michelson ...................... 606/61 |
| 6,972,019 B2 | 12/2005 | Michelson ...................... 606/61 |
| 6,974,478 B2 | 12/2005 | Reiley et al. ............... 623/17.11 |
| 6,981,975 B2 | 1/2006 | Michelson |
| 7,011,685 B2 | 3/2006 | Arnin et al. |
| 7,025,789 B2 | 4/2006 | Chow et al. ................ 623/21.11 |
| 7,041,105 B2 | 5/2006 | Michelson ...................... 606/71 |
| 7,041,135 B2 | 5/2006 | Michelson ................. 623/17.11 |
| 7,041,136 B2 | 5/2006 | Goble et al. ............... 623/17.11 |
| 7,044,952 B2 | 5/2006 | Michelson ...................... 606/71 |
| 7,048,736 B2 | 5/2006 | Robinson et al. ............... 606/61 |
| 7,063,701 B2 | 6/2006 | Michelson ...................... 606/73 |
| 7,063,702 B2 | 6/2006 | Michelson ...................... 606/73 |
| 7,074,237 B2 | 7/2006 | Goble et al. ............... 623/17.11 |
| 7,077,844 B2 | 7/2006 | Michelson ...................... 606/71 |
| 7,081,120 B2 | 7/2006 | Li et al. |
| 7,087,083 B2 | 8/2006 | Pasquet et al. |
| 7,087,084 B2 | 8/2006 | Reiley ....................... 623/17.11 |
| 7,090,698 B2 | 8/2006 | Goble et al. ............... 623/17.11 |
| 7,097,645 B2 | 8/2006 | Michelson ...................... 606/71 |
| 7,097,648 B1 | 8/2006 | Globerman et al. |
| 7,101,375 B2 | 9/2006 | Zucherman et al. ............ 606/61 |
| 7,101,398 B2 | 9/2006 | Dooris et al. .............. 623/13.11 |
| 7,112,202 B2 | 9/2006 | Michelson ...................... 606/71 |
| 7,115,130 B2 | 10/2006 | Michelson ...................... 606/71 |
| 7,163,558 B2 | 1/2007 | Senegas et al. |
| 7,163,561 B2 | 1/2007 | Michelson ................. 623/17.16 |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 * | 12/2007 | Zucherman et al. ....... 623/17.11 |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 2001/0016743 A1 | 8/2001 | Zucherman et al. |
| 2001/0018614 A1 | 8/2001 | Bianchi |
| 2002/0133155 A1 | 9/2002 | Ferree |
| 2002/0143331 A1 | 10/2002 | Zucherman et al. |
| 2002/0151895 A1 | 10/2002 | Soboleski |
| 2002/0183756 A1 | 12/2002 | Michelson |
| 2003/0040746 A1 | 2/2003 | Mitchell |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0006391 A1 | 1/2004 | Reiley |
| 2004/0010312 A1 | 1/2004 | Enayati |
| 2004/0010316 A1 | 1/2004 | William et al. |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0087947 A1 | 5/2004 | Lim et al. |
| 2004/0087948 A1 | 5/2004 | Suddaby |
| 2004/0097931 A1 | 5/2004 | Mitchell |
| 2004/0116927 A1 | 6/2004 | Graf |
| 2004/0122427 A1 | 6/2004 | Holmes |
| 2004/0133204 A1 | 7/2004 | Davies |
| 2004/0133280 A1 | 7/2004 | Trieu |
| 2004/0143268 A1 | 7/2004 | Falahee |
| 2004/0167625 A1 | 8/2004 | Beyar et al. |
| 2004/0181229 A1 | 9/2004 | Michelson |
| 2004/0186475 A1 | 9/2004 | Falahee |
| 2004/0199255 A1 | 10/2004 | Mathieu et al. |
| 2004/0210313 A1 | 10/2004 | Michelson |
| 2004/0230201 A1 | 11/2004 | Yuan |
| 2004/0230304 A1 | 11/2004 | Yuan |
| 2004/0236334 A1 | 11/2004 | Michelson |
| 2004/0236335 A1 | 11/2004 | Michelson |
| 2004/0260397 A1 | 12/2004 | Lambrecht et al. |
| 2005/0010293 A1 | 1/2005 | Zucherman et al. |
| 2005/0027297 A1 | 2/2005 | Michelson |
| 2005/0027298 A1 | 2/2005 | Michelson |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 * | 9/2005 | Hawkins et al. ................. 606/61 |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Feree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Brueneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |

| | | | | | | |
|---|---|---|---|---|---|---|
| 2006/0264938 A1 | 11/2006 | Zucherman et al. | DE | 201 12 123 U1 | 9/2001 | |
| 2006/0271044 A1 | 11/2006 | Petrini et al. | DE | 101 35 771 A1 | 2/2003 | |
| 2006/0271049 A1 | 11/2006 | Zucherman et al. | EP | 140790 A2 | 10/1984 | |
| 2006/0271061 A1 | 11/2006 | Beyar et al. | EP | 146347 A1 | 12/1984 | |
| 2006/0282079 A1 | 12/2006 | Labrom et al. | EP | 322334 A1 | 12/1988 | |
| 2006/0293662 A1 | 12/2006 | Boyer, II et al. | EP | 0307241 B1 | 12/1992 | |
| 2006/0293663 A1 | 12/2006 | Walkenhorst et al. | EP | 0677277 A2 | 10/1995 | |
| 2007/0005064 A1 | 1/2007 | Anderson et al. | EP | 0767636 B1 | 4/1997 | |
| 2007/0032790 A1 | 2/2007 | Aschmann et al. | EP | 1004276 A1 | 5/2000 | |
| 2007/0043362 A1 | 2/2007 | Malandain et al. | EP | 1011464 B1 | 6/2000 | |
| 2007/0073289 A1 | 3/2007 | Kwak et al. | EP | 1138268 A1 | 10/2001 | |
| 2007/0100340 A1 | 5/2007 | Lange et al. | EP | 1148850 B1 | 10/2001 | |
| 2007/0123861 A1 | 5/2007 | Dewey et al. | EP | 1148851 B1 | 10/2001 | |
| 2007/0142915 A1 | 6/2007 | Altarac et al. | EP | 1302169 A1 | 4/2003 | |
| 2007/0151116 A1 | 7/2007 | Malandain | EP | 1330987 A1 | 7/2003 | |
| 2007/0162000 A1 | 7/2007 | Perkins | EP | 1552797 A2 | 7/2005 | |
| 2007/0167945 A1 | 7/2007 | Lange et al. | EP | 1854433 A1 | 11/2007 | |
| 2007/0173822 A1 | 7/2007 | Bruneau et al. | EP | 1905392 A1 | 4/2008 | |
| 2007/0173823 A1 | 7/2007 | Dewey et al. | EP | 1982664 A1 | 10/2008 | |
| 2007/0191833 A1 | 8/2007 | Bruneau et al. | FR | 2623085 | 5/1989 | |
| 2007/0191834 A1 | 8/2007 | Bruneau et al. | FR | 2625097 A1 | 6/1989 | |
| 2007/0191837 A1 | 8/2007 | Trieu | FR | 2681525 A1 | 3/1993 | |
| 2007/0191838 A1 | 8/2007 | Bruneau et al. | FR | 2700941 A1 | 8/1994 | |
| 2007/0198091 A1 | 8/2007 | Boyer et al. | FR | 2703239 A1 | 10/1994 | |
| 2007/0225807 A1 | 9/2007 | Phan et al. | FR | 2705227 | 11/1994 | |
| 2007/0233068 A1 | 10/2007 | Bruneau et al. | FR | 2707864 A1 | 1/1995 | |
| 2007/0233074 A1 | 10/2007 | Anderson et al. | FR | 2717066 | 9/1995 | |
| 2007/0233076 A1 | 10/2007 | Trieu | FR | 2717068 | 9/1995 | |
| 2007/0233081 A1 | 10/2007 | Pasquet et al. | FR | 2717675 | 9/1995 | |
| 2007/0233089 A1 | 10/2007 | DiPoto et al. | FR | 2722087 A1 | 1/1996 | |
| 2007/0250060 A1 | 10/2007 | Anderson et al. | FR | 2722088 | 1/1996 | |
| 2007/0270823 A1 | 11/2007 | Trieu et al. | FR | 2722980 A1 | 2/1996 | |
| 2007/0270824 A1 | 11/2007 | Lim et al. | FR | 2724554 | 3/1996 | |
| 2007/0270825 A1 | 11/2007 | Carls et al. | FR | 2725892 A1 | 4/1996 | |
| 2007/0270826 A1 | 11/2007 | Trieu et al. | FR | 2730156 A1 | 8/1996 | |
| 2007/0270827 A1 | 11/2007 | Lim et al. | FR | 2731643 A1 | 9/1996 | |
| 2007/0270828 A1 | 11/2007 | Bruneau et al. | FR | 2775183 A1 | 8/1999 | |
| 2007/0270829 A1 | 11/2007 | Carls et al. | FR | 2780269 A1 | 12/1999 | |
| 2007/0270834 A1 | 11/2007 | Bruneau et al. | FR | 2782911 A1 | 3/2000 | |
| 2007/0270874 A1 | 11/2007 | Anderson | FR | 2799948 A1 | 4/2001 | |
| 2007/0272259 A1 | 11/2007 | Allard et al. | FR | 2806614 A1 | 9/2001 | |
| 2007/0276368 A1 | 11/2007 | Trieu et al. | FR | 2806616 A1 | 9/2001 | |
| 2007/0276369 A1 | 11/2007 | Allard et al. | FR | 2816197 A1 | 5/2002 | |
| 2007/0276493 A1 | 11/2007 | Malandain et al. | GB | 780652 | 8/1957 | |
| 2007/0276496 A1 | 11/2007 | Lange et al. | JP | 02-224660 | 9/1990 | |
| 2007/0276497 A1 | 11/2007 | Anderson | JP | 09-075381 | 3/1997 | |
| 2007/0282443 A1 | 12/2007 | Globerman et al. | JP | 10-179622 | 7/1998 | |
| 2008/0021457 A1 | 1/2008 | Anderson et al. | SU | 988281 | 1/1983 | |
| 2008/0021460 A1 | 1/2008 | Bruneau et al. | SU | 1484348 A1 | 6/1989 | |
| 2008/0058934 A1 | 3/2008 | Malandain et al. | WO | WO 90/00037 | 1/1990 | |
| 2008/0114357 A1 | 5/2008 | Allard et al. | WO | WO 91/16018 | 10/1991 | |
| 2008/0114358 A1 | 5/2008 | Anderson et al. | WO | WO 94/21185 | 9/1994 | |
| 2008/0114456 A1 | 5/2008 | Dewey et al. | WO | WO 94/26192 | 11/1994 | |
| 2008/0147190 A1 | 6/2008 | Dewey et al. | WO | WO 94/26193 | 11/1994 | |
| 2008/0161818 A1 | 7/2008 | Kloss et al. | WO | WO 94/26195 | 11/1994 | |
| 2008/0167685 A1 | 7/2008 | Allard et al. | WO | WO 95/35067 | 12/1995 | |
| 2008/0183209 A1 | 7/2008 | Robinson et al. | WO | WO 96/08206 A1 | 3/1996 | |
| 2008/0183211 A1 | 7/2008 | Lamborne et al. | WO | WO 96/39975 | 12/1996 | |
| 2008/0183218 A1 | 7/2008 | Mueller et al. | WO | WO 97/18769 | 5/1997 | |
| 2008/0215094 A1 | 9/2008 | Taylor | WO | WO 98/20939 | 5/1998 | |
| 2008/0221685 A9 | 9/2008 | Altarac et al. | WO | WO 98/48717 | 11/1998 | |
| 2008/0234824 A1 | 9/2008 | Youssef et al. | WO | WO 98/55038 | 12/1998 | |
| 2008/0262617 A1 | 10/2008 | Froehlich et al. | WO | WO 99/26562 | 6/1999 | |
| 2008/0281360 A1 | 11/2008 | Vittur et al. | WO | WO 99/40866 | 8/1999 | |
| 2008/0281361 A1 | 11/2008 | Vittur et al. | WO | WO 99/42051 | 8/1999 | |
| 2009/0062915 A1 | 3/2009 | Kohm et al. | WO | WO 99/56653 | 11/1999 | |
| 2009/0105766 A1 | 4/2009 | Thompson et al. | WO | WO 99/59669 | 11/1999 | |
| 2009/0105773 A1 | 4/2009 | Lange et al. | WO | WO 00/04851 | 2/2000 | |
| 2009/0234389 A1 | 9/2009 | Chuang et al. | WO | WO 00/13619 | 3/2000 | |
| 2009/0270918 A1 | 10/2009 | Attias et al. | WO | WO 00/13620 | 3/2000 | |
| 2010/0121379 A1 | 5/2010 | Edmond | WO | WO 00/38582 | 7/2000 | |
| | | | WO | WO 00/44319 | 8/2000 | |
| | FOREIGN PATENT DOCUMENTS | | WO | WO 00/53126 | 9/2000 | |
| DE | 2821678 A1 | 4/1980 | WO | WO 01/26566 A1 | 4/2001 | |
| DE | 3113142 A1 | 1/1982 | WO | WO 01/28442 A1 | 4/2001 | |
| DE | 3922044 A1 | 2/1991 | WO | WO 01/54598 A1 | 8/2001 | |
| DE | 4012622 C1 | 7/1991 | WO | WO 02/34120 A2 | 5/2002 | |
| DE | 4409833 | 10/1995 | WO | WO 02/051326 | 7/2002 | |
| DE | 4414781 | 11/1995 | WO | WO 02/085226 A1 | 10/2002 | |

| | | |
|---|---|---|
| WO | WO 03/057055 A1 | 7/2003 |
| WO | WO 03/101350 A1 | 12/2003 |
| WO | WO 2004/047689 A1 | 6/2004 |
| WO | WO 2004/047691 A1 | 6/2004 |
| WO | WO 2004/071358 A1 | 8/2004 |
| WO | WO 2004/084768 A2 | 10/2004 |
| WO | WO 2004/098465 A1 | 11/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Tsuji, Haruo, et al., "Ceramic Interspinous Block (CISB) Assisted Anterior Interbody Fusion," Journal of Spinal Disorders, vol. 3, No. 1, pp. 77-86, Raven Press, Ltd., New York (1990).

Porter, Richard W., "Spinal Stenosis and Neurogenic Claudication," SPINE, vol. 21, No. 17, pp. 2046-2052, Lippincott-Raven Publishers (1996).

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertebral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochirurgia, Advanced Peripheral Nerve Surgery and Minimal Invasive Spinal Surgery, Alexandre et al., eds., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

INTERSPINOUS PROCESS IMPLANT HAVING DEPLOYABLE WING AND METHOD OF IMPLANTATION

CLAIM OF PRIORITY

U.S. Provisional Patent Application No. 60/663,885 entitled INTERSPINOUS PROCESS IMPLANT HAVING DEPLOYABLE WING AND METHOD OF IMPLANTATION by Zucherman et al., filed Mar. 21, 2005.

CROSS-REFERENCE TO RELATED APPLICATIONS

This U.S. patent application incorporates by reference all of the following co-pending applications and issued patents:

U.S. Patent Application Ser. No. 60/663,918, entitled "Interspinous Process Implant Having Deployable Wing and Method of Implantation," filed concurrently;

U.S. patent application Ser. No. 10/850,267, entitled "Distractible Interspinous Process Implant and Method of Implantation," filed May 20, 2004;

U.S. Pat. No. 6,419,676, entitled "Spine Distraction Implant and Method," issued Jul. 16, 2002 to Zucherman, et al.;

U.S. Pat. No. 6,451,019, entitled "Supplemental Spine Fixation Device and Method," issued Sep. 17, 2002 to Zucherman, et al.;

U.S. Pat. No. 6,582,433, entitled "Spine Fixation Device and Method," issued Jun. 24, 2003 to Yun;

U.S. Pat. No. 6,652,527, entitled "Supplemental Spine Fixation Device and Method," issued Nov. 25, 2003 to Zucherman, et al;

U.S. Pat. No. 6,695,842, entitled "Interspinous Process Distraction System and Method with Positionable Wing and Method," issued Feb. 24, 2004 to Zucherman, et al;

U.S. Pat. No. 6,699,246, entitled "Spine Distraction Implant," issued Mar. 2, 2004 to Zucherman, et al; and U.S. Pat. No. 6,712,819, entitled "Mating Insertion Instruments for Spinal Implants and Methods of Use," issued Mar. 30, 2004 to Zucherman, et al.

TECHNICAL FIELD

This invention relates to interspinous process implants.

BACKGROUND OF THE INVENTION

The spinal column is a bio-mechanical structure composed primarily of ligaments, muscles, vertebrae and intervertebral disks. The bio-mechanical functions of the spine include: (1) support of the body, which involves the transfer of the weight and the bending movements of the head, trunk and arms to the pelvis and legs, (2) complex physiological motion between these parts, and (3) protection of the spinal cord and the nerve roots.

As the present society ages, it is anticipated that there will be an increase in adverse spinal conditions which are characteristic of older people. By way of example only, with aging comes an increase in spinal stenosis (including, but not limited to, central canal and lateral stenosis), and facet arthropathy. Spinal stenosis results in a reduction foraminal area (i.e., the available space for the passage of nerves and blood vessels) which compresses the nerve roots and causes radicular pain. Humpreys, S. C. et al., Flexion and traction effect on C5-C6 foraminal space, Arch. Phys. Med. Rehabil., vol. 79 at 1105 (September 1998). Another symptom of spinal stenosis is myelopathy, which results in neck and back pain and muscle weakness. Id. Extension and ipsilateral rotation of the neck and back further reduces the foraminal area and contributes to pain, nerve root compression and neural injury. Id.; Yoo, J. U. et al., Effect of cervical spine motion on the neuroforaminal dimensions of human cervical spine, Spine, vol. 17 at 131 (Nov. 10, 1992). In contrast, neck and back flexion increases the foraminal area. Humpreys, S. C. et al., at 1105.

Over time, loss of disk height in the thoracic and lumbar regions, as well as the cervical region can result in a degenerative cascade with deterioration of all components of a motion segment resulting in segment instability and ultimately in spinal stenosis. During the process of deterioration, disks can become herniated and/or become internally torn and chronically painful. When symptoms seem to emanate from both anterior (disk) and posterior (facets and foramen) structures, patients cannot tolerate positions of extension or flexion.

Pain associated with stenosis can be relieved by medication and/or surgery. It is desirable to eliminate the need for major surgery for all individuals, and in particular, for the elderly.

Accordingly, a need exists to develop spine implants that alleviate pain caused by spinal stenosis and other such conditions caused by damage to, or degeneration of, the spine. Such implants would distract, or increase the space between, the vertebrae to increase the foraminal area and reduce pressure on the nerves and blood vessels of the spine.

A further need exists for development of a minimally invasive surgical implantation method for spine implants that preserves the physiology of the spine.

Further, a need exists for an implant that accommodates the distinct anatomical structures of the spine, minimizes further trauma to the spine, and obviates the need for invasive methods of surgical implantation. Additionally, a need exists to address adverse spinal conditions that are exacerbated by spinal extension.

DETAILED DESCRIPTION

Interspinous Implants

Figure 1A:
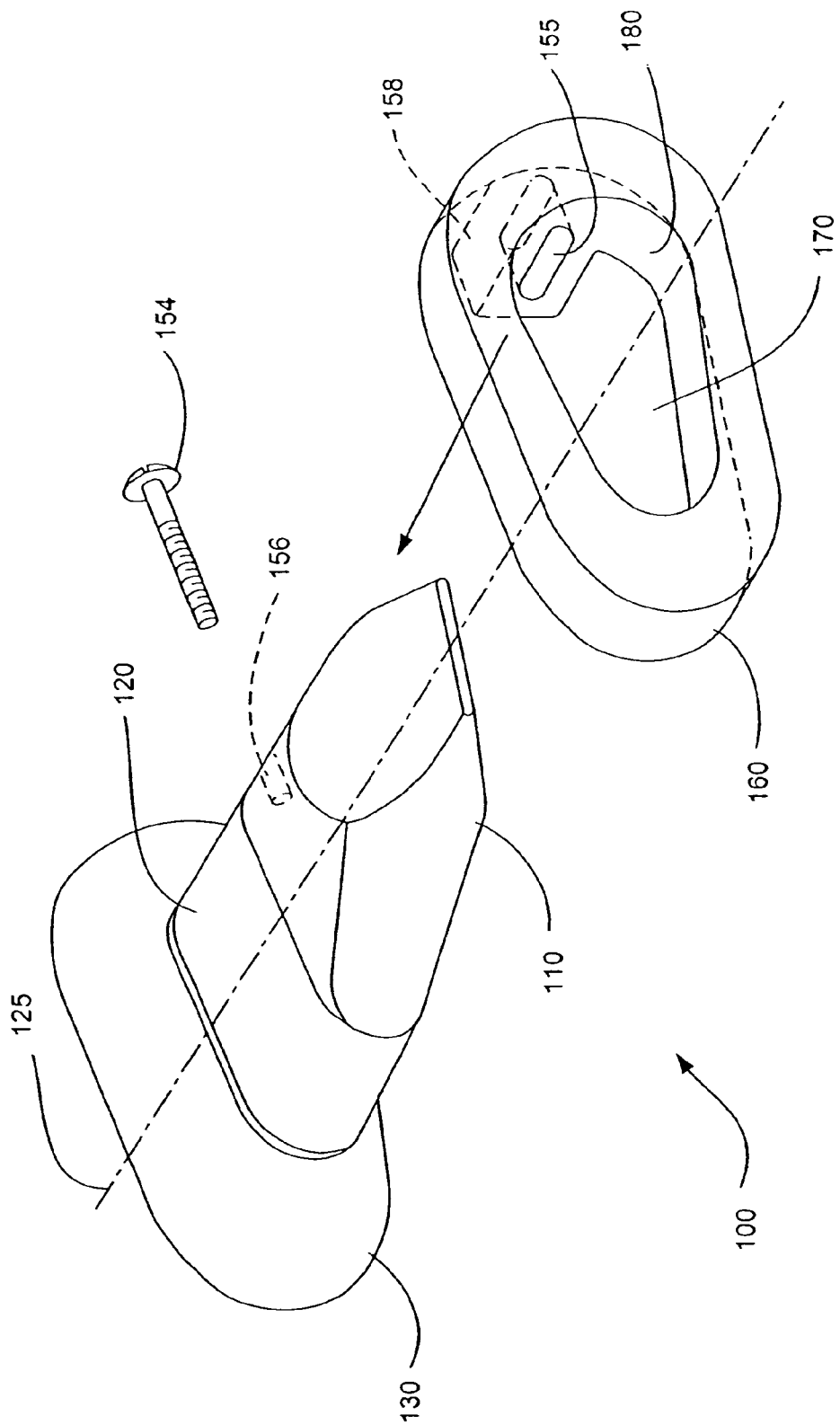
FIG. 1A is a perspective view of an implant including a spacer having a tear-drop shaped cross-section, a distraction guide, a first wing, and a second wing connectable with the distraction guide.

FIG. 1A is a perspective view of an implant as described in U.S. patent application Ser. No. 10/850,267, filed May 20, 2004, incorporated herein by reference. The implant 100 comprises a first wing 130, a spacer 120, and a lead-in tissue expander (also referred to herein as a distraction guide) 110. The distraction guide 110 in this particular embodiment is wedge-shaped, i.e., the implant has an expanding cross-section from a proximal end of the implant 100 to a region where the guide 110 joins with the spacer 120 (referencing for the figures is based on the point of insertion of the implant between spinous processes). As such, the distraction guide 110 functions to initiate distraction of the soft tissue and the spinous processes when the implant 100 is surgically inserted between the spinous processes. It is to be understood that the distraction guide 110 can be pointed and the like, in order to facilitate insertion of the implant 100 between the spinous processes of adjacent cervical vertebrae. It is advantageous that the insertion technique disturb as little of the bone and surrounding tissue or ligaments as possible in order to reduce trauma to the site and promote early healing, and prevent destabilization of the normal anatomy. For embodiments such as those of FIGS. 1A and 1B, there is no requirement to remove any of the bone of the spinous processes and no requirement to sever, or remove from the body, ligaments and tissues immediately associated with the spinous processes. For example, it is unnecessary to sever the supraspinal ligament of the lower vertebrae or the ligamentum nuchae (which corresponds to the supraspinal ligament) which partially cushions the spinous processes of the upper cervical vertebrae.

As can be seen, the spacer 120 can be teardrop-shaped in cross-section perpendicular to a longitudinal axis 125 of the implant 100. In this way, the shape of the spacer 120 can roughly conform to a wedge-shaped space, or a portion of the space, between adjacent spinous processes within which the implant 100 is to be positioned. As shown in FIG. 1A, the spacer 120 (and the first wing 130) is shaped to accommodate the anatomical form or contour of spinous processes (and/or laminae) of preferably the C6 and C7 vertebra for placement between such spinous processes (i.e., the C6-C7 motion segment). The same shape or variations of this shape can be used to accommodate other motion segments, for example in the thoracic or lumbar regions. In other embodiments the spacer 120 can have alternative shapes such as circular, wedge, oval, ovoid, football, and rectangular with rounded corners, and other shapes. The shape of the spacer 120 can be selected for a particular patient so that the physician can position the implant 100 as close as possible to the anterior portion of the surface of the spinous process. The shape selected for the spacer 120 can affect the contact surface area of the implant 100 and the spinous processes that are to be subject to distraction. Increasing the contact surface area between the implant 100 and the spinous processes can distribute a load force between the spinous frame and the implant 100.

The first wing 130 is likewise teardrop-shaped in cross-section perpendicular to a longitudinal axis 125 of the spacer 120 and distraction guide 110. The dimensions of the first wing 130 can be larger than that of the spacer 120, particularly along the axis of the spine, and can limit or block lateral displacement of the implant 100 in the direction of insertion along the longitudinal axis 125. As with the spacer 120, the first wing 130 can have other cross-sectional shapes, such as elliptical, wedge, circular, oval, ovoid, football, and rectangular with rounded corners and other shapes.

The implant 100 of FIG. 1A further includes an adjustable wing 160 (also referred to herein as a second wing) separate from the distraction guide 110, the spacer 120 and the first wing 130. The second wing 160 is connectable with the distraction guide 110 (and/or the spacer 120) once the implant 100 is positioned between adjacent spinous processes. The second wing 160, similar to the first wing 130, can limit or block lateral displacement of the implant 100, however displacement is limited or blocked in the direction opposite insertion. When both the first wing 130 and the second wing 160 are connected with the implant 100 and the implant 100 is positioned between adjacent spinous processes, a portion of the spinous processes can be sandwiched between the first wing 130 and the second wing 160, limiting displacement along the longitudinal axis 125. As can be seen, the second wing 160 can be teardrop-shaped in cross-section. A lip 180 defining a space 170 through the second wing 160 allows the second wing 160 to pass over the distraction guide 110 to meet and connect with the distraction guide 110 and/or the spacer 120. The second wing 160 is then secured to the distraction guide 110 and/or the spacer 120. The second wing 160, can be designed to be interference-fit onto the spacer 120 or a portion of the distraction guide 110 adjacent to the spacer 120. Where the second wing 160 is interference-fit, there is no additional attachment device to fasten the second wing 160 relative to the remainder of the implant 100.

Alternatively, various fasteners can be used to secure the second wing 160 relative to the remainder of the implant 100. For example, FIG. 1A illustrates an embodiment of an implant 100 including a teardrop-shaped second wing 160 having a tongue 158 at the posterior end of the second wing 160. A bore 155 is disposed through the tongue 158, and is aligned with a corresponding bore 156 on the spacer 120 when the second wing 160 is brought into position by surgical insertion relative to the rest of the implant 100. A threaded screw 154 can be inserted through the aligned bores 155,156 in a posterior-anterior direction to secure the second wing 160 to the spacer 120. The direction of insertion from a posterior to an anterior direction has the screw 154 engaging the bores 155,156 and the rest of the implant 100 along a direction that is generally perpendicular to the longitudinal axis 125. This orientation is most convenient when the physician is required to use a screw 154 to secure the second wing 160 to the rest of the implant 100. The second wing 160 can further be secured to the spacer 120 by some other mechanism, for example such as a flexible hinge (not shown) with a protrusion that engages an indentation of one of the distraction guide 110 and the spacer 120. Alternatively, the second wing 160 can be secured to one of the distraction guide 110 and the spacer 120 by still some other mechanism.

Figure 1B:
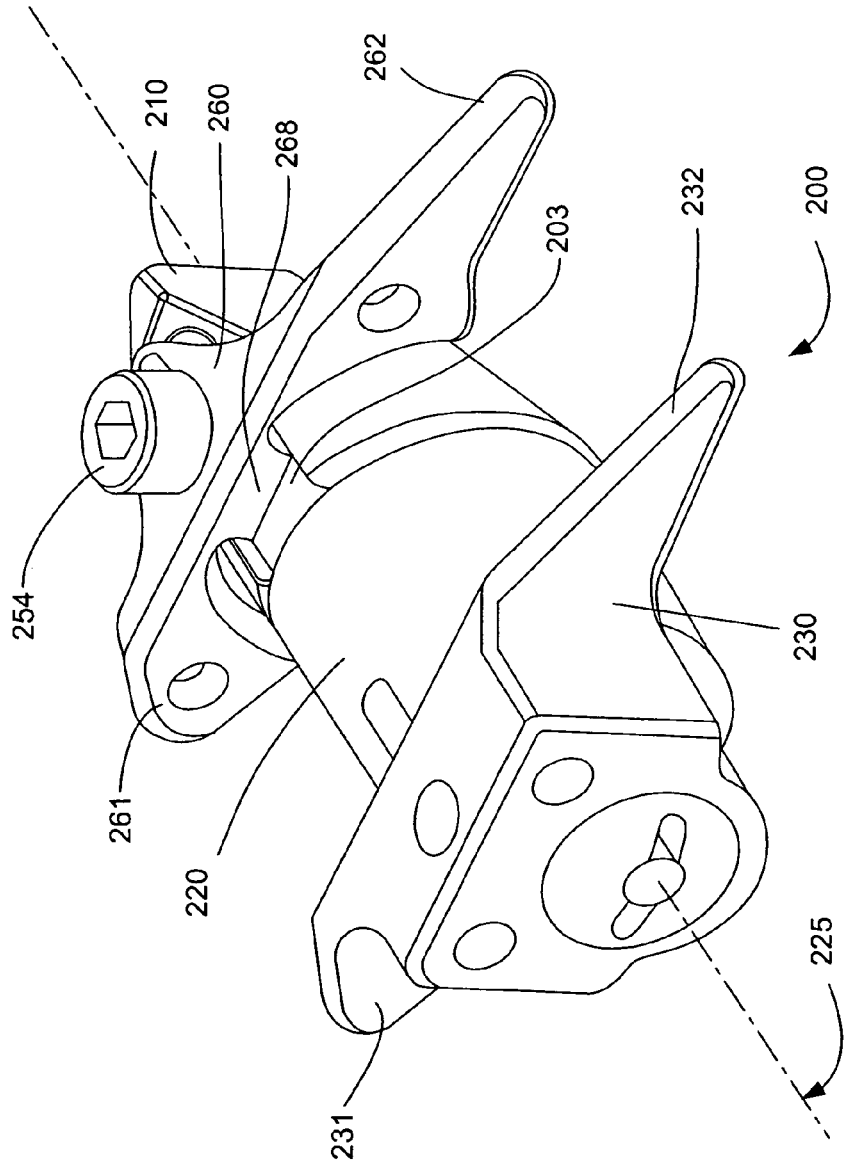
FIG. 1B is a perspective view of an implant including a rotatable spacer having an elliptical cross-section, a distraction guide, a first wing, and a second wing connectable with the distraction guide.

FIG. 1B is a perspective view of an implant as described in U.S. Pat. No. 6,695,842 to Zucherman, et al., incorporated herein by reference. The implant 200 has a main body that includes a spacer 220, a first wing 230, a lead-in tissue expander 210 (also referred to herein as a distraction guide) and an alignment track 203. The main body of the implant 200 is inserted between adjacent spinous processes and remains in place (where desired) without attachment to the bone or ligaments.

The distraction guide 210 includes a tip from which the distraction guide 210 expands, the tip having a diameter sufficiently small such that the tip can pierce an opening in an interspinous ligament and/or can be inserted into a small initial dilated opening. The diameter and/or cross-sectional area of the distraction guide 210 gradually increases until it is substantially similar to the diameter of the spacer 220. The tapered front end eases the ability of a physician to urge the implant 200 between adjacent spinous processes. When urging the main body of the implant 200 between adjacent spinous processes, the front end of the distraction guide 210 distracts the adjacent spinous processes and dilates the interspinous ligament so that a space between the adjacent spinous processes is approximately the diameter of the spacer 220.

As shown in FIG. 1B, the spacer 220 is elliptically shaped in cross-section, and can swivel so that the spacer 220 can self-align relative to the uneven surfaces of the spinous processes. Self-alignment can ensure that compressive loads are distributed across the surface of the bone. As contemplated in Zucherman '842, the spacer 220 can have, for example, a diameter of six millimeters, eight millimeters, ten millimeters, twelve millimeters and fourteen millimeters. These diameters refer to the height by which the spacer 220 distracts and maintains apart the spinous process. For an elliptically shaped spacer 220, the selected height (i.e., diameter) is the minor dimension measurement across the ellipse. The major dimension is transverse to the alignment of the spinous process, one above the other.

The first wing 230 has a lower portion 231 and an upper portion 232. The upper portion 232 is shaped to accommodate the anatomical form or contour of spinous processes (and/or laminae) of preferably the L4 (for an L4-L5 placement) or L5 (for an L5-S1 placement) vertebra. The same shape or variations of this shape can be used to accommodate other motion segments, such as motion segments in the cervical and thoracic regions. The lower portion 231 can also be rounded to accommodate the spinous processes. The lower portion 231 and upper portion 232 of the first wing 230 act as a stop mechanism when the implant 200 is inserted between adjacent spinous processes. The implant 200 cannot be inserted beyond the surfaces of the first wing 230. Additionally, once the implant 200 is inserted, the first wing 230 can prevent some side-to-side, or posterior-to-anterior movement of the implant 200.

As with the implant 100 of FIG. 1A, the implant 200 of FIG. 1B further includes a second wing 260. Similar to the first wing 230, the second wing 260 includes a lower portion 261 and an upper portion 262 sized and/or shaped to accommodate the anatomical form or contour of the spinous processes and/or lamina. The second wing 260 can be secured to the main body of the implant 200 with a fastener 254. The second wing 260 also has an alignment tab 268. When the second wing 260 is initially placed on the main body of the implant 200, the alignment tab 268 engages the alignment track 203. The alignment tab 268 slides within the alignment track 203 and helps to maintain the adjustable wing 260 substantially parallel with the first wing 230. When the main body of the implant 200 is inserted into the patient and the second wing 260 has been attached, displacement along the longitudinal axis 225 in either the direction of insertion or the direction opposite insertion can be limited or blocked. Further, the second wing 260 also can prevent some side-to-side, or posterior-to-anterior movement.

For both the implant 100 of FIG. 1A and the implant 200 of FIG. 1B, where a second wing 160,260 is connected with the implant 100,200 after the implant 100,200 is positioned between the spinous processes, a procedure for positioning such an implant 100,200 and subsequently connecting the second wing 160,260 with the implant 100,200 can require a bilateral approach wherein a physician must access both sides of the interspinous ligament, a first side to pierce and/or distract the interspinous ligament and position the implant 100,200 so that the movement in the direction of insertion is satisfactorily limited by the first wing 130,230, and a second side to attach the second wing 160,260 such that movement in the direction opposite insertion is satisfactorily limited by the second wing 160,260.

Implants Having Deployable Second Wing

Referring to FIGS. 2A through 3B, implants 300 and methods for positioning such implants in accordance with the present invention can, in an embodiment, include a deployable second wing 360 associated with a main body 301 such that the second wing 360 can be deployed with a physician needing only to access a first side of spinous processes to limit or block movement along the longitudinal axis 325.

Figure 2A:
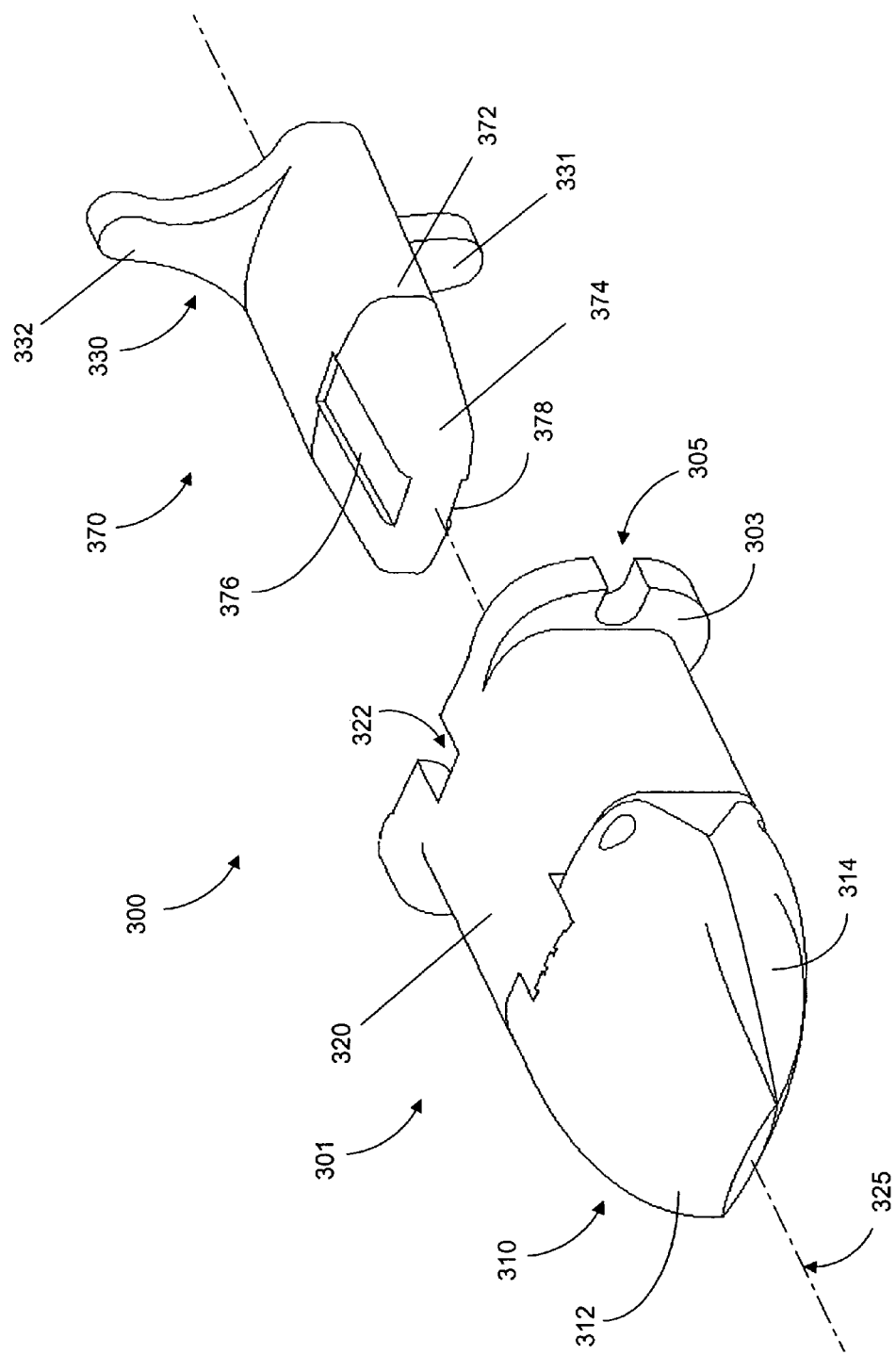
FIG. 2A is a perspective view of an implant in accordance with an embodiment of the present invention including a main body and an insert, the main body having a distraction guide, a spacer, and a first wing.
Figure 2B:
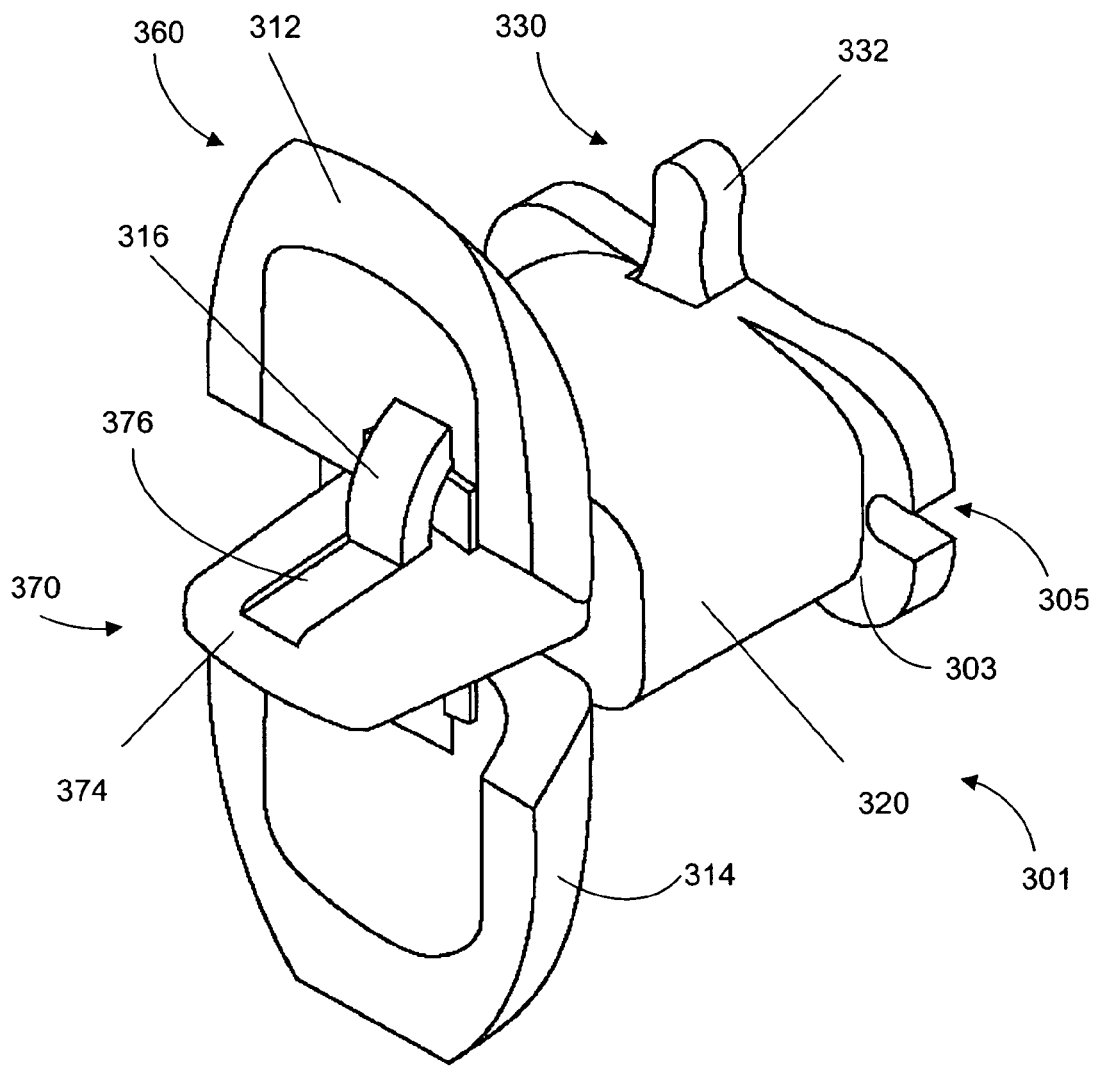
FIG. 2B is a perspective view of the implant of FIG. 2A wherein the insert is positioned within the main body, causing the distraction guide associated with the main body to limit or block movement of the implant when positioned between adjacent spinous processes.

As shown in FIG. 2A, the implant 300 includes a main body 301 having a fixed spacer 320 and a distraction guide 310. The distraction guide 310 comprises a first winglet (also referred to herein as an upper winglet) 312 and a second winglet (also referred to herein as a lower winglet) 314, and when arranged in a first configuration can include a tip from which the distraction guide 310 expands, the tip having a diameter sufficiently small such that the tip can pierce an opening in an interspinous ligament and between spinous processes and/or can be inserted into a small initial dilated opening. The diameter and/or cross-sectional area of the distraction guide 310 is then gradually increased until it is substantially similar to the diameter of the spacer 320. In this respect, the distraction guide 310 of FIG. 2A can resemble a distraction guide as described above when arranged in the first configuration. The winglets 312,314 can be hinged or otherwise pivotably connected with the main body 301 such that the winglets 312,314 can be arranged in a second configuration (FIG. 2B) once the implant 300 is positioned between spinous processes. In a second configuration one or both of the winglets 312,314 abut at least one of the spinous processes and/or related tissues when urged in a direction opposite from insertion, thereby limiting motion along the longitudinal axis 325. Thus when arranged in a second configuration, the distraction guide 310 becomes a second wing 360, as shown in FIG. 2B.

The implant 300 includes an insert 370 having an insert body 372 and a first wing 330. As shown in FIG. 2B, the insert 370 can be mated with the main body 301 to arrange the distraction guide 310 of the implant 300 in the second configuration, thereby deploying the second wing 360. To facilitate mating of the main body 301 and the insert 370, the spacer 320 includes a cavity sized and shaped for receiving the insert body 372 and accessible from a distal end of the main body 301. A portion of the upper winglet 312 and the lower winglet 314 can extend at least partially into the cavity so that when the insert body 372 is received within the cavity, the insert body 372 displaces the portions, causing the distraction guide 310 to be arranged in the second configuration. In the embodiment shown, the upper winglet 312 and the lower winglet 314 each include a lever 316,318 comprising a curved protrusion that protrudes into the cavity when the distraction guide 310 is in the first configuration. As the insert body 372 of the insert 370 fills the cavity, the insert body 372 contacts the first lever 316 and the second lever 318, applying a force to the first lever 316 and the second lever 318 which translates into a pivoting motion of the hinged upper winglet 312 and the hinged lower winglet 314. The insert body 372 can optionally have a tapered proximal end 374 having a first groove 376 and a second groove 378 corresponding to the first lever 316 and the second lever 318, respectively. The tapered shape of the proximal end 374 allows the upper winglet 312 and lower winglet 314 to be deployed gradually, fully deploying as the insert body 372 is fully seated within the cavity. The main body 301 is shown including a flange 303 in which is formed notches 305 to receive an insertion tool (not shown), for example. As the insert body 372 is seated within the cavity, an upper tab 332 and a lower tab 331 of the first wing 330 seats within cut-outs 322 of the flange 303.

Figure 3A:
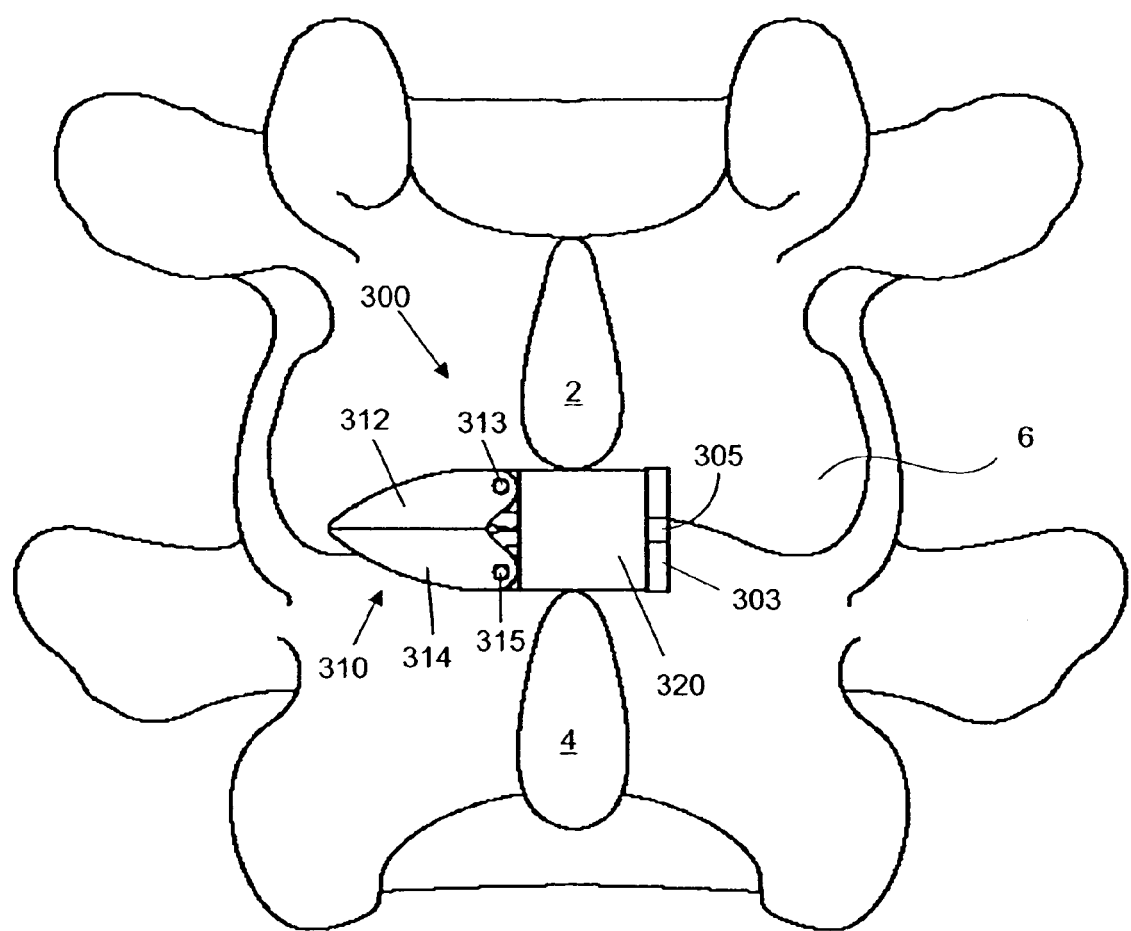
FIG. 3A is a side view of the main body of the implant of FIGS. 2A and 2B positioned between adjacent spinous processes.

Referring to FIG. 3A, the main body 301 of the implant 300 is shown positioned between adjacent spinous processes of the targeted motion segment. The motion segment shown is within the lumbar region, but in other embodiments, particularly where a fixed spacer 320 is used, implants 300 in accordance with the present convention can be positioned at motion segments of the thoracic and cervical region. The main body 301 is positioned as shown by initially approaching the interspinous ligament between the upper and lower adjacent spinous processes 2,4 through an opening to the right of the interspinous ligament, roughly posterior to the right inferior articular facet 6 of the vertebrae from which the upper spinous process 2 extends. The main body 301 can be associated with one or more insertion tools (not shown), and the distraction guide 310 can be arranged in the first configuration. The tip of the distraction guide 310 is positioned roughly adjacent to a point along the interspinous ligament, and the distraction guide 310 is then urged through the interspinous ligament, piercing the interspinous ligament and/or separating and distracting fibers of the interspinous ligaments. The main body 301 is then urged through the interspinous ligament until the spacer 320 is positioned between the adjacent spinous processes 2,4 so that the spacer 320 supports a load applied by the spinous processes 2,4.

Figure 3B:
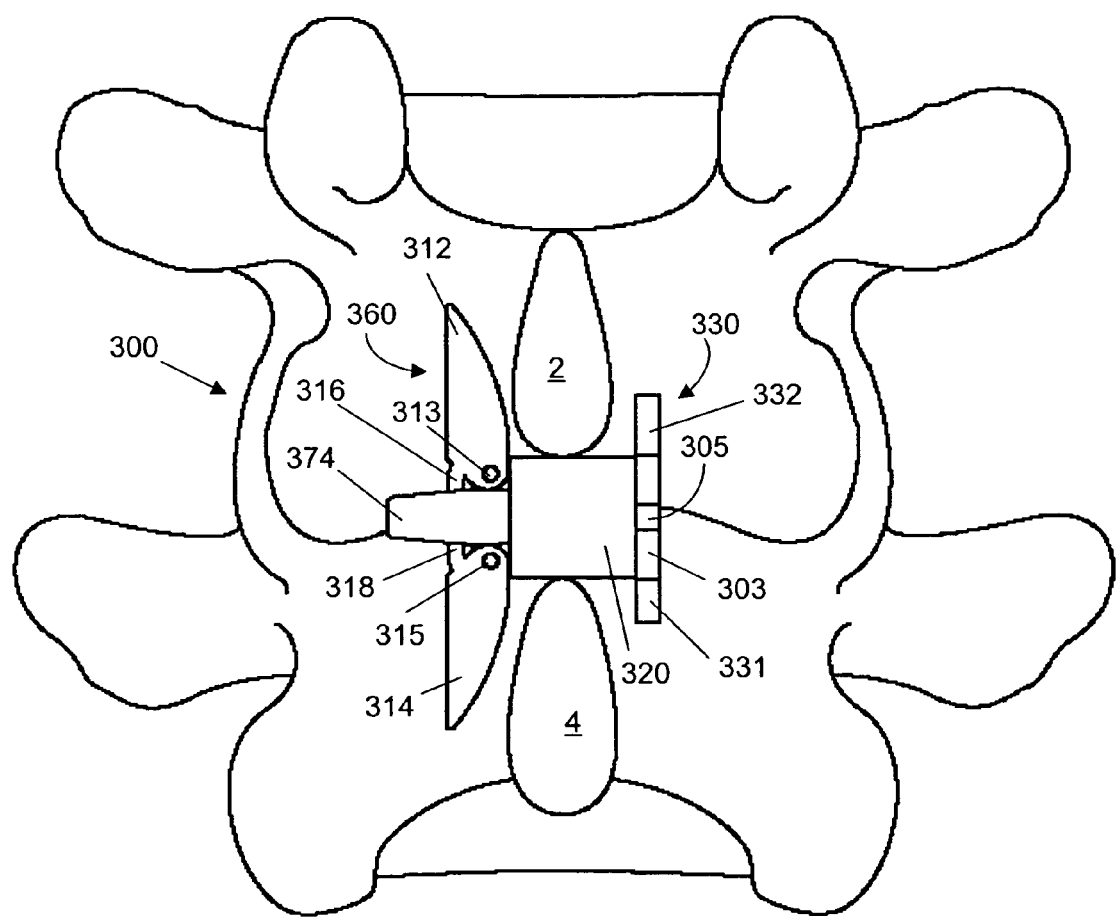
FIG. 3B is a side view of the implant of FIG. 3A wherein the insert is positioned within the main body.

Referring to FIG. 3B, once the implant 300 is positioned as desired, the insertion tools can be removed from the opening and the insert 370 can be positioned at the distal end of the main body 301. The insert body 372 can be urged into the cavity within the main body 301 until the proximal end 374 of the insert body 372 contacts the first lever 316 and the second lever 318. The insert 370 can then be further urged along the longitudinal axis 325 so that the insert body 372 urges the first lever 316 and the second lever 318 away from the insert body 372, causing the upper winglet 312 and the lower winglet 314 to pivot about the first hinge 313 and the second hinge 315, respectively. As the first lever 316 and the second lever 318 are displaced from the cavity, the first lever 316 and the second lever 318 are guided along corresponding grooves 376,378 of the tapered proximal end 374. As the insert body 372 seats within the cavity of the main body 301, the upper winglet 312 and the lower winglet 314 deploy as a second wing 360. The insertion tool can be removed from the incision once the insert body 372 is seated within the main body 301. As can be seen a portion of the upper spinous process and a portion of the lower spinous process are sandwiched between the first wing 330 and the second wing 360, limiting motion along the longitudinal axis 325.

Implants and methods for positioning such implants between spinous processes in accordance with the present invention are not meant to be limited to embodiments as described above and otherwise herein, but rather are meant to include any implant having a second wing deployable by urging an insert within a main body positioned between adjacent spinous processes. Myriad different variations may be readily apparent to one of ordinary skill in the art. For example, in an alternative embodiment, the main body 301 of the implant 300 of FIGS. 2A through 3B can include a lower winglet 314 pivotably associated with the main body 301 while an upper winglet 312 is fixedly associated with the main body 301. An insert 370 can be adapted to deploy only the lower winglet 314 when seated within the cavity of the main body 301.

In other embodiments, a first wing 310 can extend from the main body 301 rather than, or in addition to, a first wing extending from the insert 370. When the main body 301 is initially positioned between the adjacent spinous processes, movement of the main body 301 along the longitudinal axis 325 can be limited in the direction of insertion. As the first wing 3-1-0 extending from the main body 301 contacts one or both of the adjacent spinous processes, further movement of the main body 301 in the direction of insertion can be limited or blocked. The first wing can thus act as a hard stop, allowing the main body 301 to be positioned without requiring a position of the main body 301 along the spinous processes to be estimated, thereby easing implantation.

Figure 4:
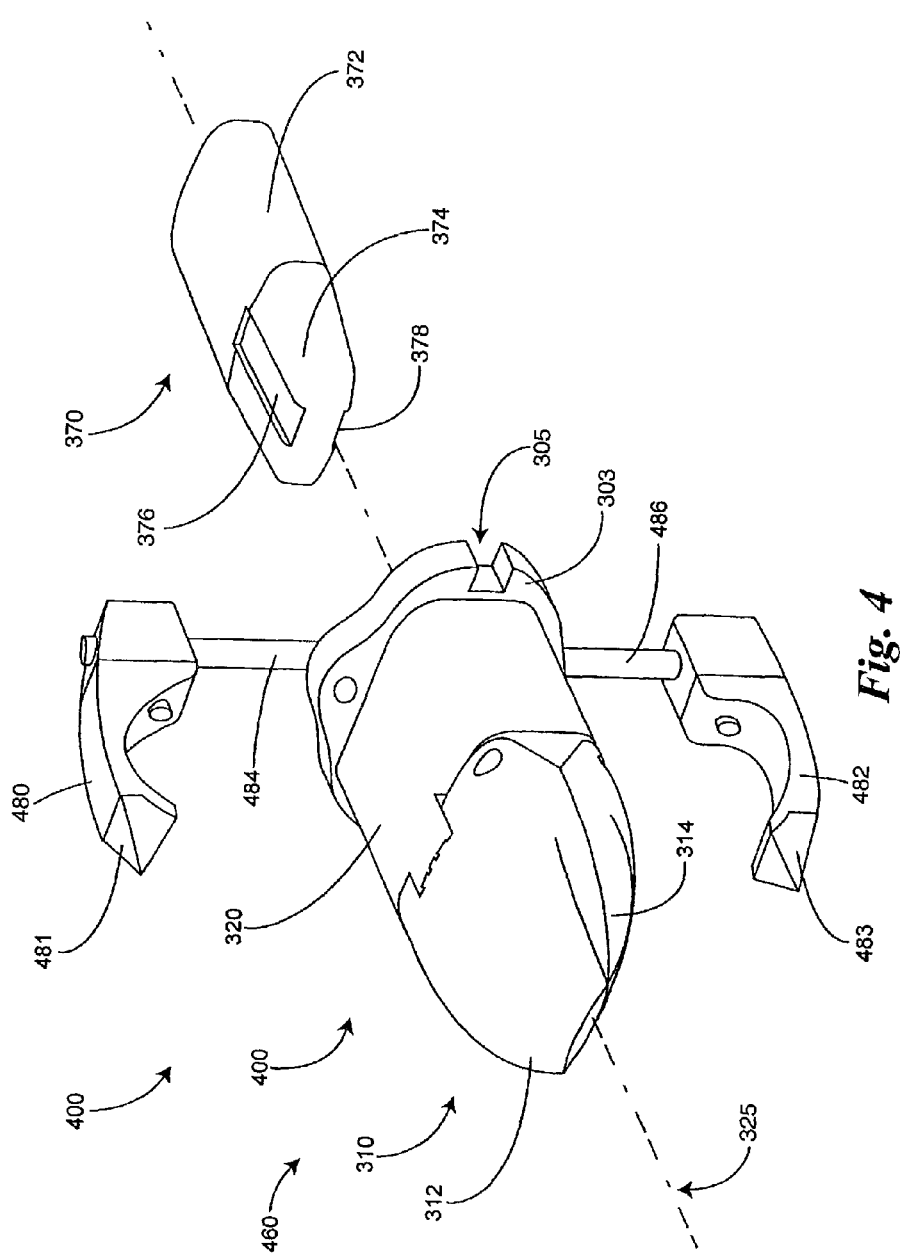
FIG. 4 is a perspective view of an implant in accordance with an alternative embodiment wherein the main body includes hooks to limit relative movement of adjacent spinous processes during flexion motion.

Referring to FIG. 4, in still further embodiments implants 400 in accordance with the present invention can include one or both of a first engagement element (also referred to herein as an upper hook) 480 and a second engagement element (also referred to herein as a lower hook) 482 for limiting flexion motion in a motion segment. For example, similar hooks have been described in greater detail in U.S. Pat. No. 6,451,019 issued Sep. 17, 2002 to Zucherman et al. and U.S. Pat. No. 6,652,527 issued Nov. 25, 2003 to Zucherman et al., both incorporated herein by reference. Implants in accordance with the present invention can include such arrangements. The implant 400 shown in FIGS. 4 and 5 includes an upper hook 480 extending from an upper connection rod 484 rotatably associated with the main body 401 and a lower hook 482 extending from a lower connection rod 486 rotatably associated with the main body 401. Alternatively, the connection rods 484,486 can be fixedly associated with the main body 401. The hooks 480,482 include tapered proximal ends 481, 483 that act as lead-in tissue expanders to distract interspinous ligaments of the motion segments above and below the targeted motion segment. As the main body 401 is positioned between adjacent spinous processes, the tapered proximal ends 481,483 of the upper and lower hooks 480,482 can likewise pierce and/or distract interspinous ligaments so that the upper and lower hooks 480,482 can be properly positioned to limit or restrain flexion motion of the targeted motion segment when the main body 401 is in place. As shown, the hooks 480,482 can be pivotably associated with the connection rods 484,486 so that the hooks 480,482 can be rotated relative to the connection rods 484,486, thereby allowing a physician to improve contact and spread loads between the hooks 480,482 and corresponding spinous processes 2,4. The rotatable upper connection rod 484 and lower connection rod 486 can provide flexibility in placement, so that where an anatomy varies between patients and varies between motion segments such that the arrangement of a minor dimension and major dimension of the implant 400 about the longitudinal axis 325 varies, the implant 400 can be accommodated.

Figure 5:
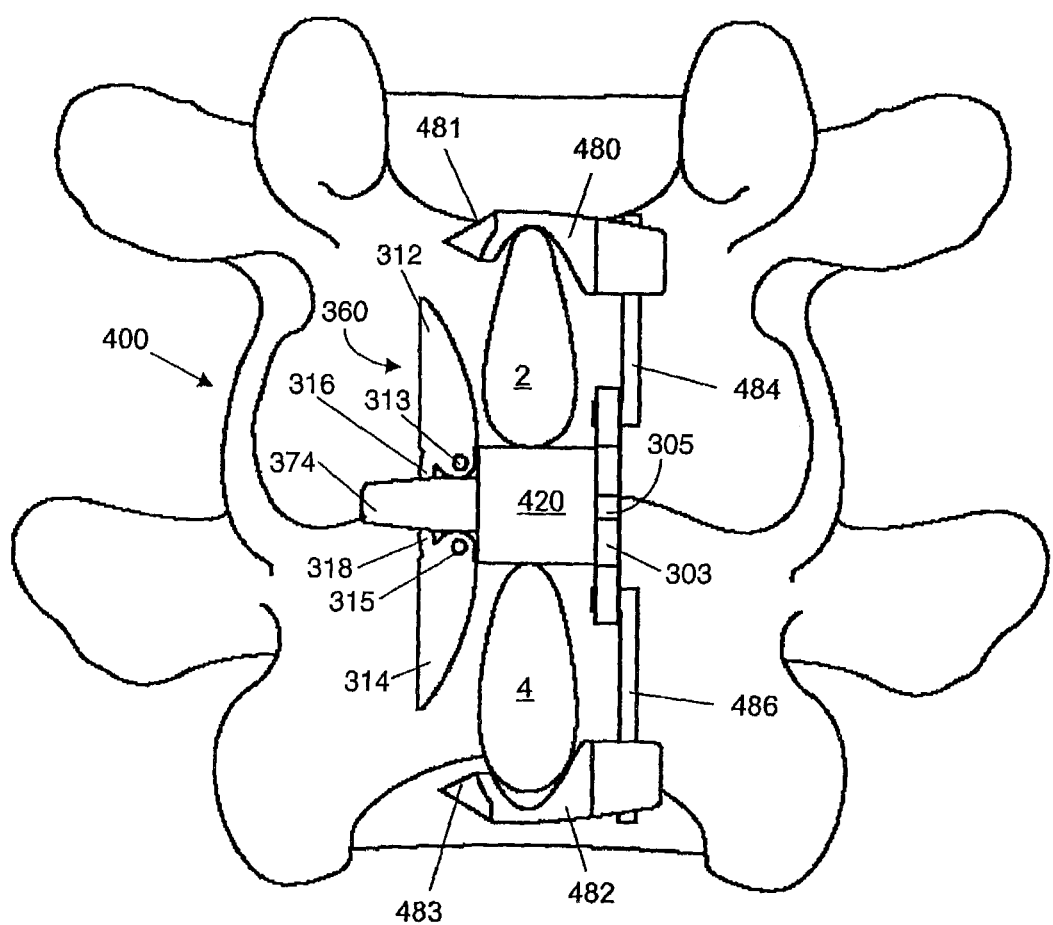
FIG. 5 is a side view of the implant of FIG. 4 positioned between adjacent spinous processes and arranged so that the hooks confine the adjacent spinous processes.

FIG. 5 is a posterior view of the implant 400 positioned between adjacent spinous processes 2,4 and having an upper hook 480 and a lower hook 482 arranged so that both flexion and extension is limited as desired. Further, the second wing 360 is deployed to limit movement of the implant 400 along the longitudinal axis 325. The upper hook 480 and the lower hook 482 prevent movement along the longitudinal axis 325 in the direction opposite insertion, making a first wing unnecessary.

Figure 6A:
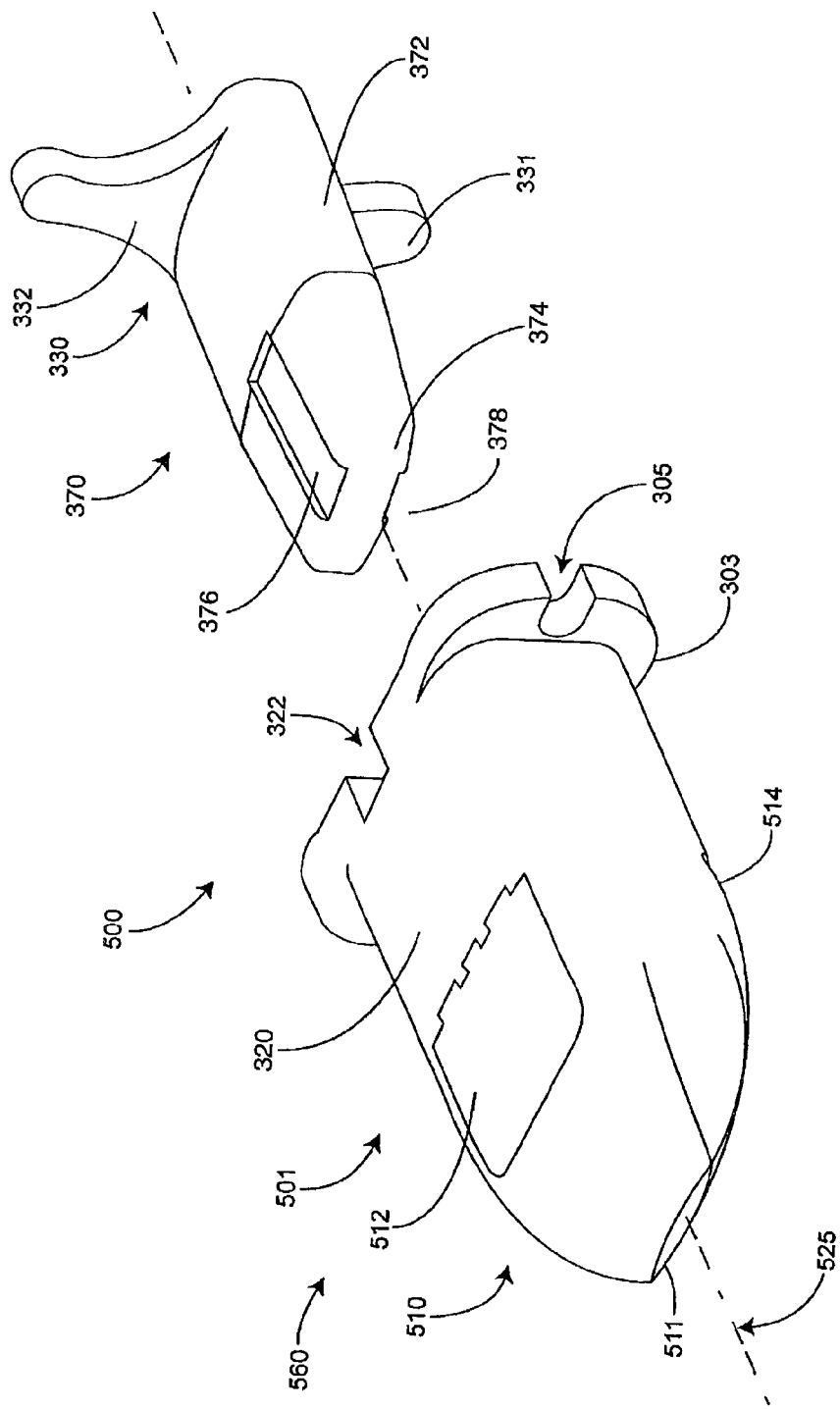
FIG. 6A is a perspective view of still another embodiment of an implant in accordance with the present invention, wherein a first section and a second section of a distraction guide are deployable to form a second wing.
Figure 6B:
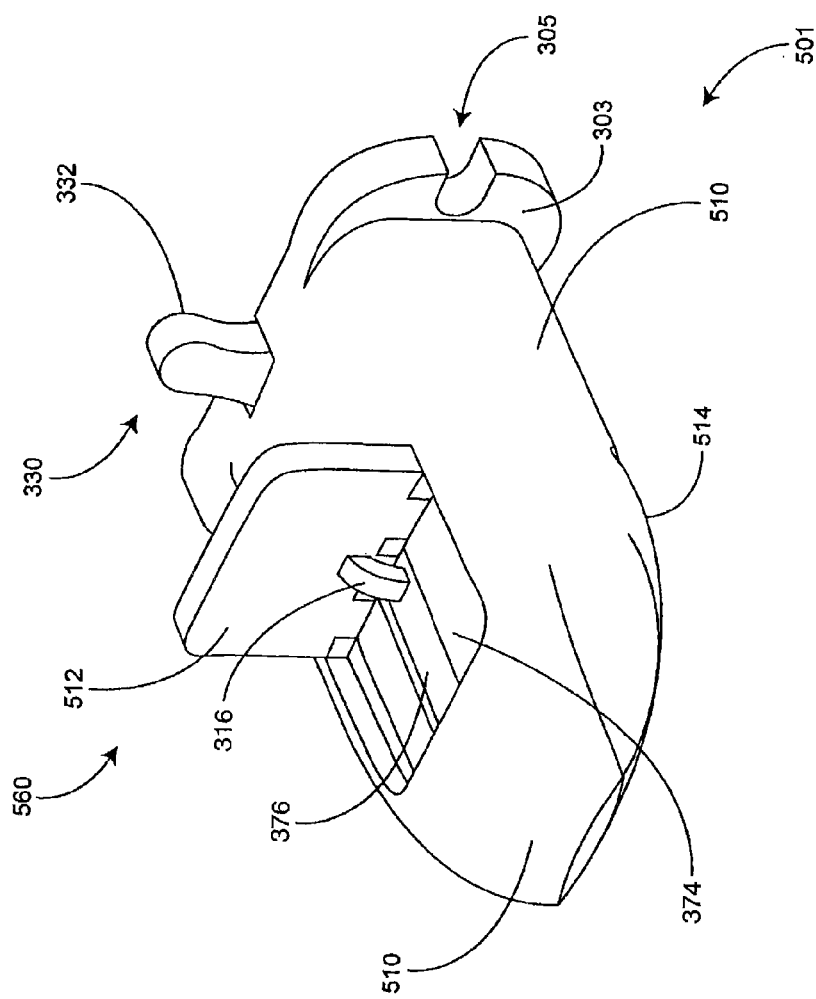
FIG. 6B is a perspective view of the implant of FIG. 6A wherein the insert is positioned within the main body, causing the first section and the second section of the distraction guide to deploy.

Referring to FIGS. 6A and 6B, in still other embodiments implants 500 and methods for positioning such implants 500 between spinous processes in accordance with the present invention can include a distraction guide 510 wherein portions of the distraction guide 510 can be extended from the distraction guide 510 to form an upper winglet 512 and a lower winglet 514, respectively, of a second wing 560 by positioning an insert 370 within a cavity of the main body 501. This is in contrast to the above embodiment where the entire distraction guide is formed by the winglets. In this embodiment, the winglet 512,514 extend out the side of the distraction guide 510. When not extended, as seen in FIG. 6A, the winglet 512,514 partially form the sides of the distraction guide 510. Such embodiments are contemplated to be useful where it is desired that the second wing 560 have a limited height relative to implants 300,400 as described above where the entire distraction guide 310 is deployed (see FIGS. 2A through 3B). For example, where implants 500 are to be positioned at adjacent motion segments, it can be desired that the second wings 560 of the implants 500 do not interfere with one another implant, for example during an extension motion when compressive loads are applied to the implants 500. As with implants described above, one of ordinary skill in the art can appreciate the myriad different variations of the implant 500 of FIGS. 6A and 6B. For example, in alternative embodiments the upper winglet 512 and the lower winglet 514 can have some other shape. For example, the positions of the upper winglet 512 and lower winglet 514 are staggered so that implants 500 positioned at adjacent motion segments can be more easily positioned without interfering with one another. Such staggering can also accommodate anatomies where one of the upper and lower spinal processes is wider than the other. With staggering, for example, the upper winglet 512 can be pivotably mounted on the distraction guide 510 at a position less distant from the distraction end 511 than the location where the lower winglet 514 is pivotably mounted on the distraction guide 510. In still other embodiments, the upper winglet 512 and the lower winglet 514 can have some other shape.

Figure 7A:
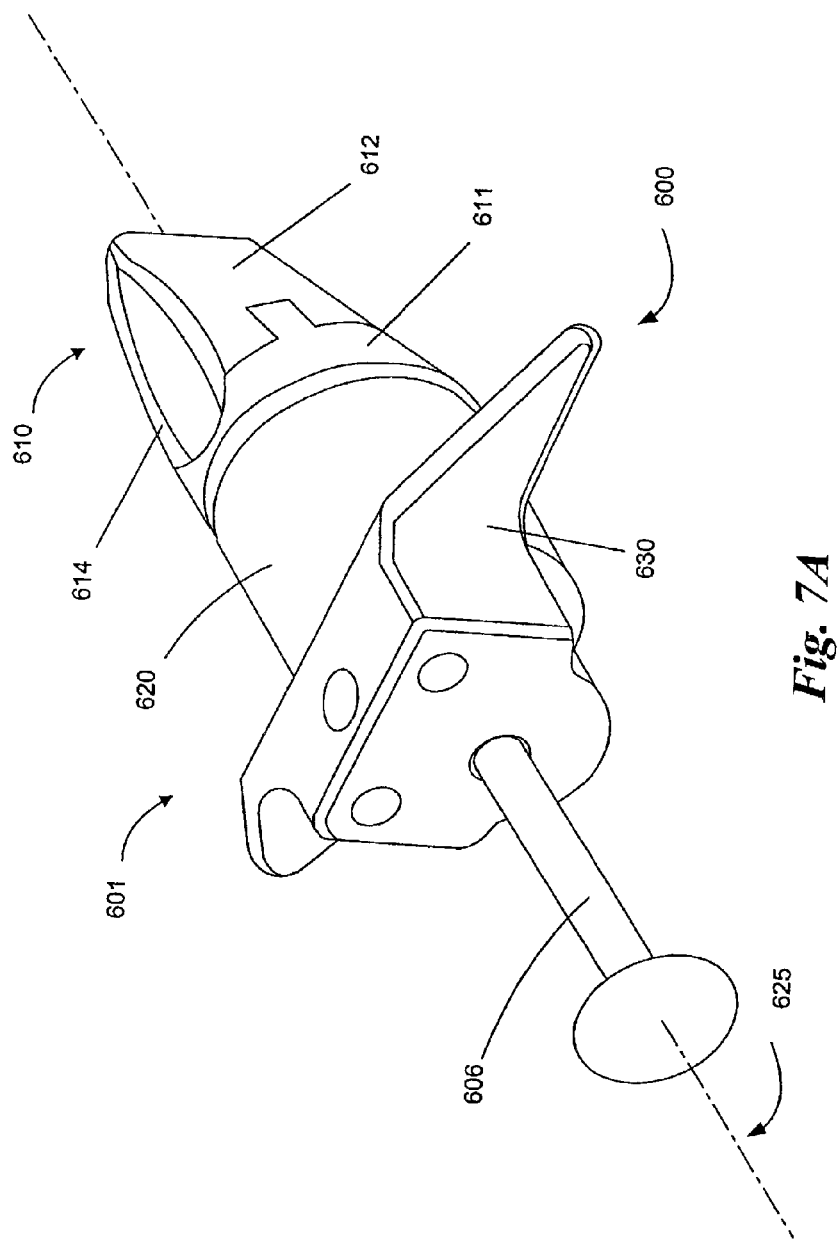
FIG. 7A is a perspective view of a still further embodiment of an implant in accordance with the present invention including a rotatable spacer.
Figure 7B:
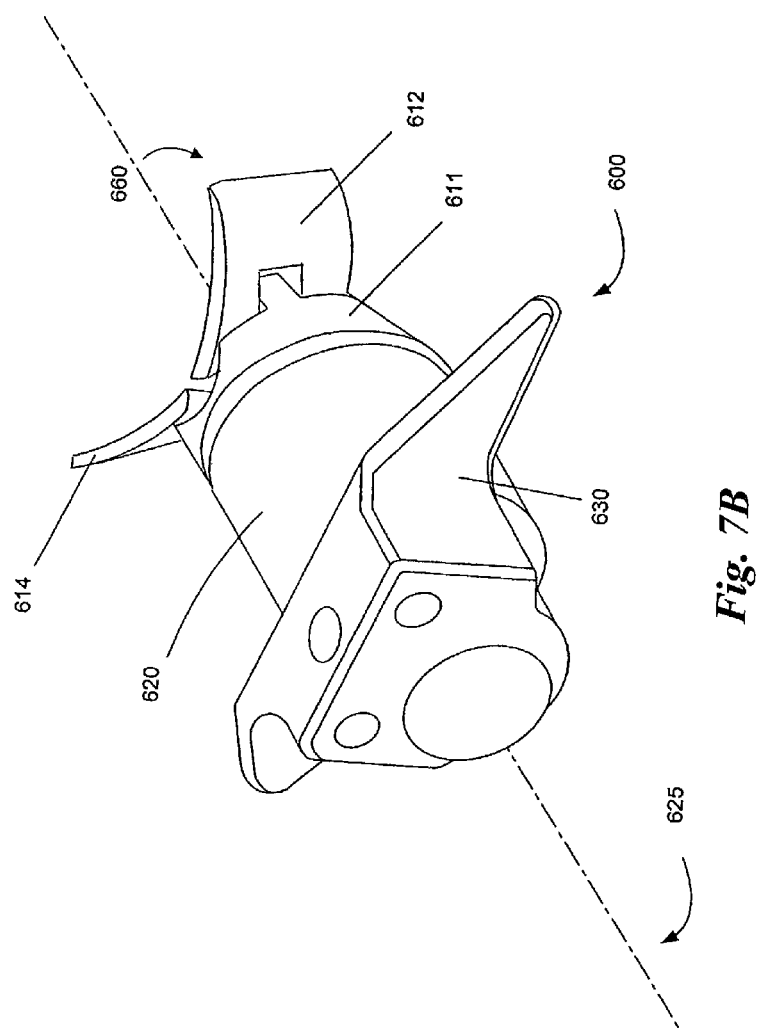
FIG. 7B is a perspective view of the implant of FIG. 7A wherein the insert is positioned within a central body so that the distraction guide deploys as a second wing.
Figure 7C:
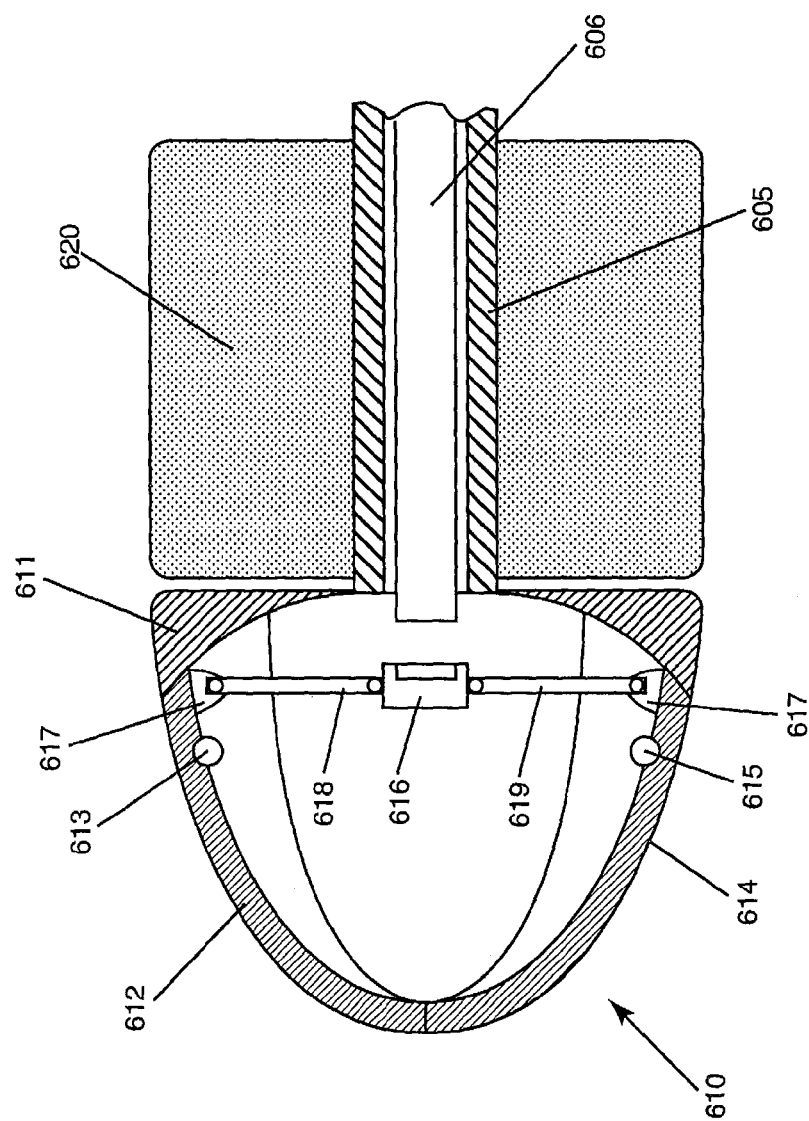
FIG. 7C is a cross-sectional side view of distraction guide of FIG. 7A.
Figure 7D:
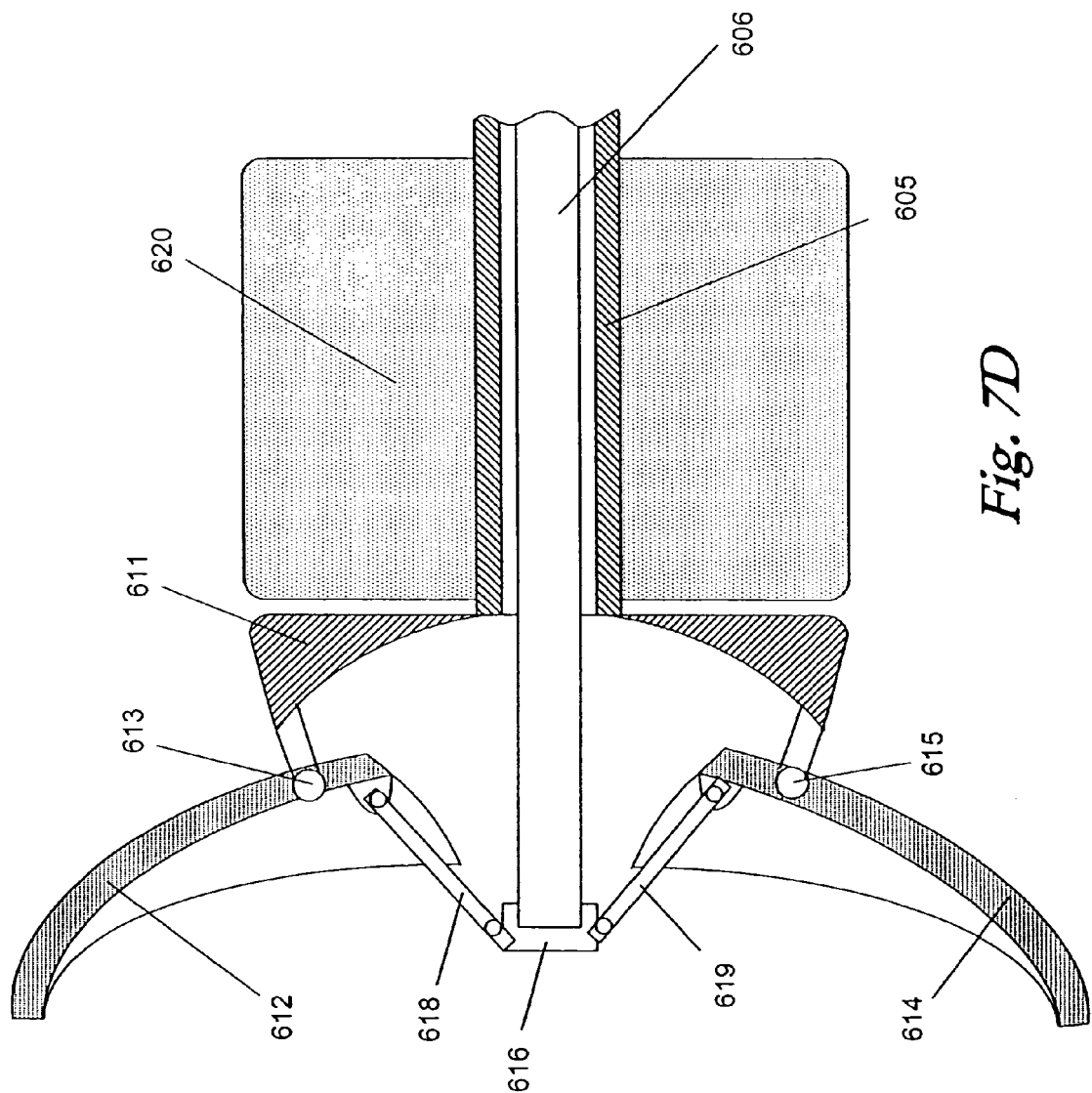
FIG. 7D is a cross-sectional side view of distraction guide of FIG. 7B.
Figure 8:
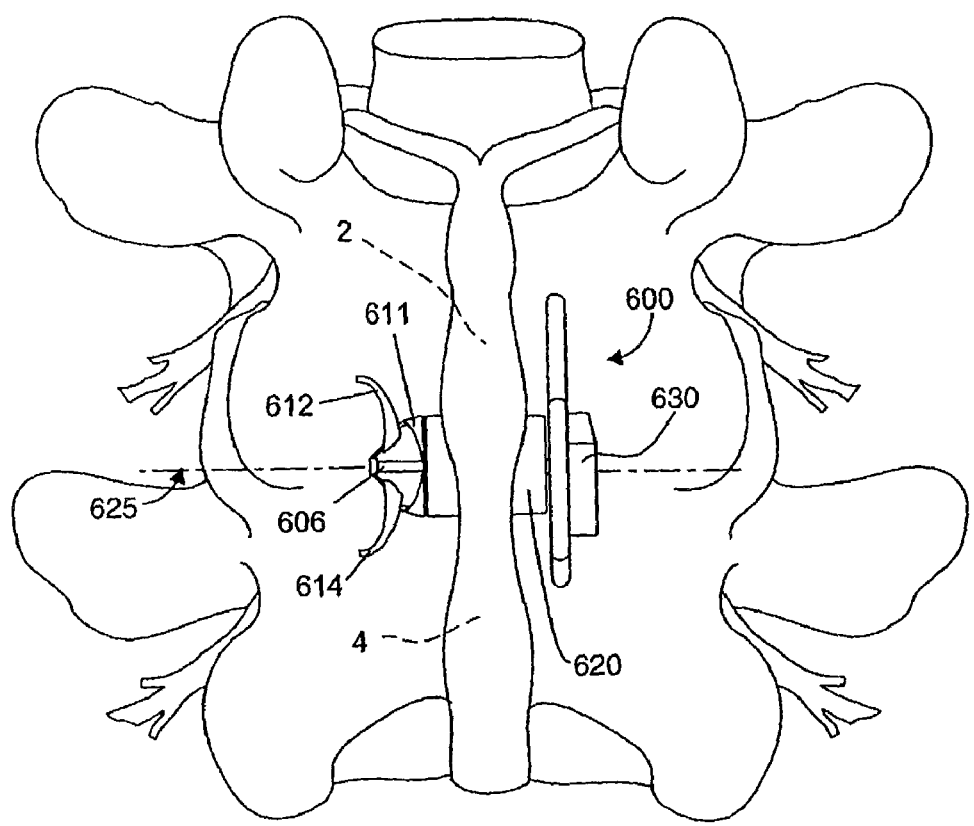
FIG. 8 is a side view of the implant of FIGS. 7A-7D positioned between adjacent spinous processes.

Referring to FIGS. 7A through 8, in still further embodiments of implants 600 in accordance with the present invention, the main body 601 can include a hollow central body 605 (shown in FIGS. 7C and 7D) extending from a first wing 630. A rotatable spacer 620 is disposed about the hollow central body 605. The implant 600 can include a spacer 620 that resembles spacers, for example, as described above in FIG. 1B. A distraction guide 610 can extend from the hollow central body 605 and can include an upper winglet 612 and a lower winglet 614, one or both of which can be pivotably associated with a main portion 611 of the distraction guide 610 so that the upper winglet 612 and/or the lower winglet 614 can be deployed as a second wing 660. A pin 606 can be inserted into the hollow central body 605 to deploy the second wing 630. Referring to FIG. 7B, once the pin 606 is seated within the main body 601, the upper winglet 612 and the lower winglet 614 can be pivoted away from each other so that the upper winglet 612 and the lower winglet 614 limit or block motion along the longitudinal axis 625 in the direction opposite from insertion. The upper winglet 612 and the lower winglet 614 thus act as a second wing 660.

Referring to the partial cross-sections of FIGS. 7C and 7D, in an embodiment the distraction guide 610 can include a cup 616 structure sized and arranged to receive the pin 606. Bar structures 618,619 can be pivotably connected between the cup structure 616 and one or both of the upper winglet 612 and the lower winglet 614 so that when a force is applied to the cup structure 616 by the pin 606, the force is further transferred to the upper winglet 612 and the lower winglet 614, causing the upper winglet 612 and the lower winglet 614 to pivot on hinges 613,615 associated with the main portion 611 of the distraction guide 610 so that the second wing 660 is deployed. As can be seen, the pivot points 613,615 of the upper winglet 612 and the lower winglet 614 are arranged proximally relative to the mount points 617 of the bar structures 618,619, causing the upper winglet 612 and the lower winglet 614 to pivot away from one another when the mount points 617 are urged together by the insertion of the pin 606 (as seen in FIG. 7D). In other embodiments, the upper winglet 612 and the lower winglet 614 can be caused to pivot away from one another using some other mechanism. Implants in accordance with the present invention are not intended to be limited to such second wing deployment mechanisms as are described in detail herein.

Referring to FIG. 8, the implant 600 is shown positioned between adjacent spinous processes 2,4. The second wing 660 as shown is sized such that when arranged in a first configuration (i.e., as a distraction guide 610) the upper winglet 612 and the lower winglet 614 do not extend undesirably into the adjacent tissues. However, the upper winglet 612 and the lower winglet 614 can be sized and shaped other than as shown in FIG. 8. The upper winglet 612 and the lower winglet 614 need only be sized and shaped such that when arranged in a second configuration, the upper and lower winglets 612,614 limit or block movement along the longitudinal axis 625 in a direction opposite from insertion.

Figure 9A:
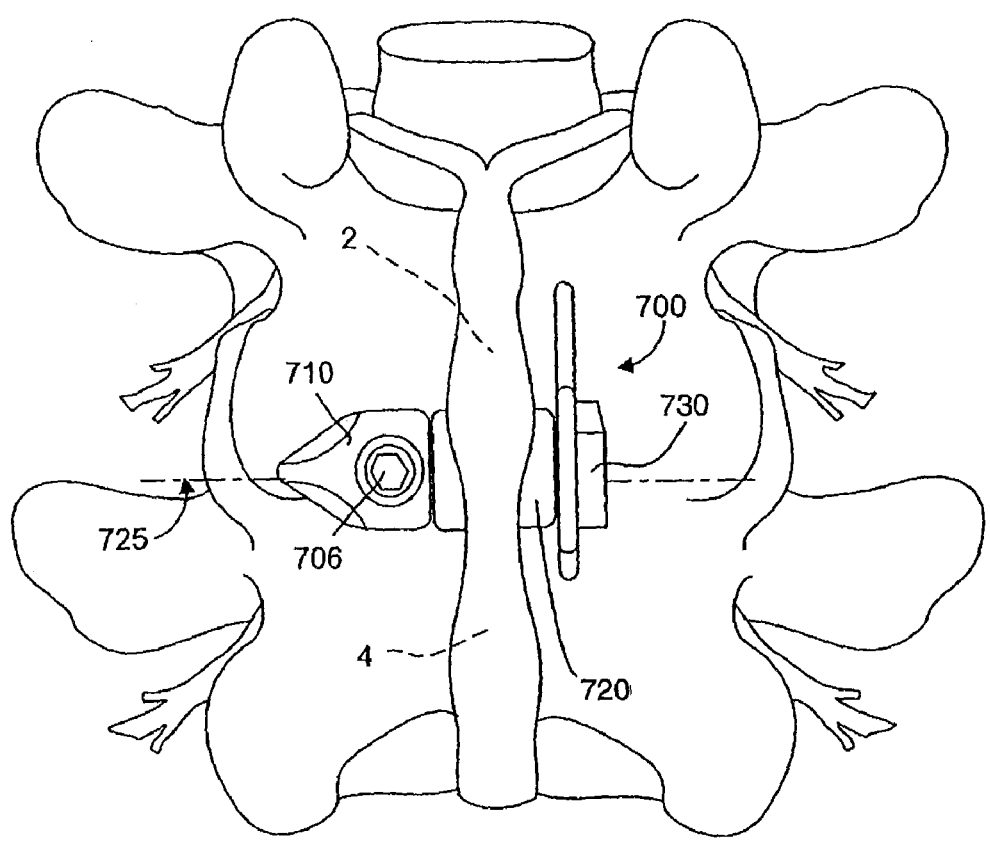
FIG. 9A is a side view of an alternative embodiment of the implant positioned between adjacent spinous processes.
Figure 9B:
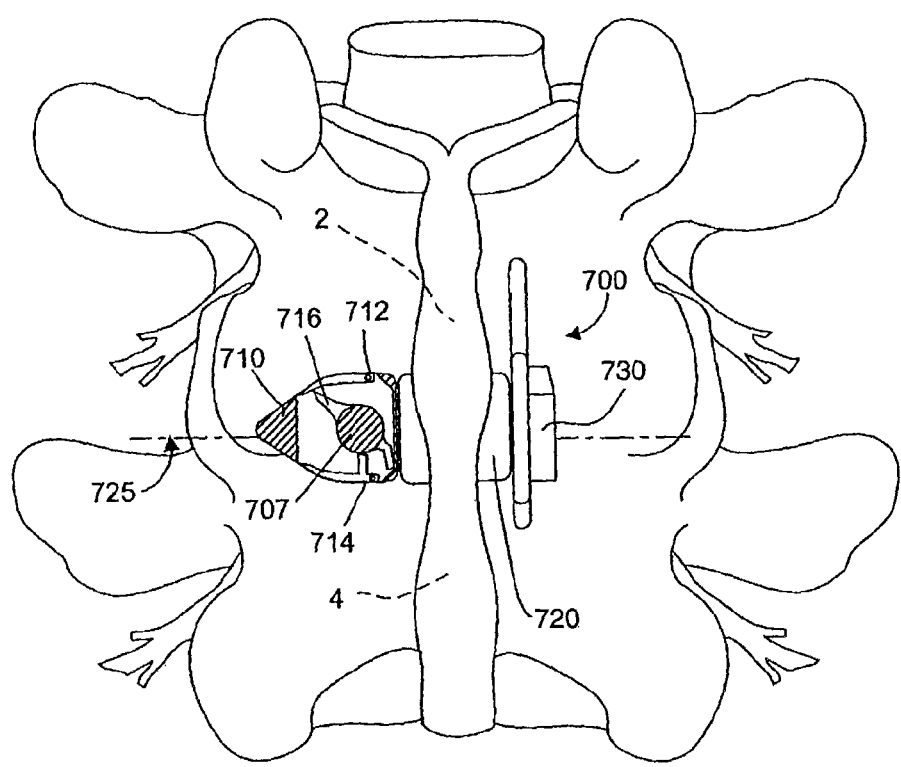
FIG. 9B is a partial cross-section side view of the implant of FIG. 9A showing deployable winglets disposed within a distraction guide of the implant.
Figure 9C:
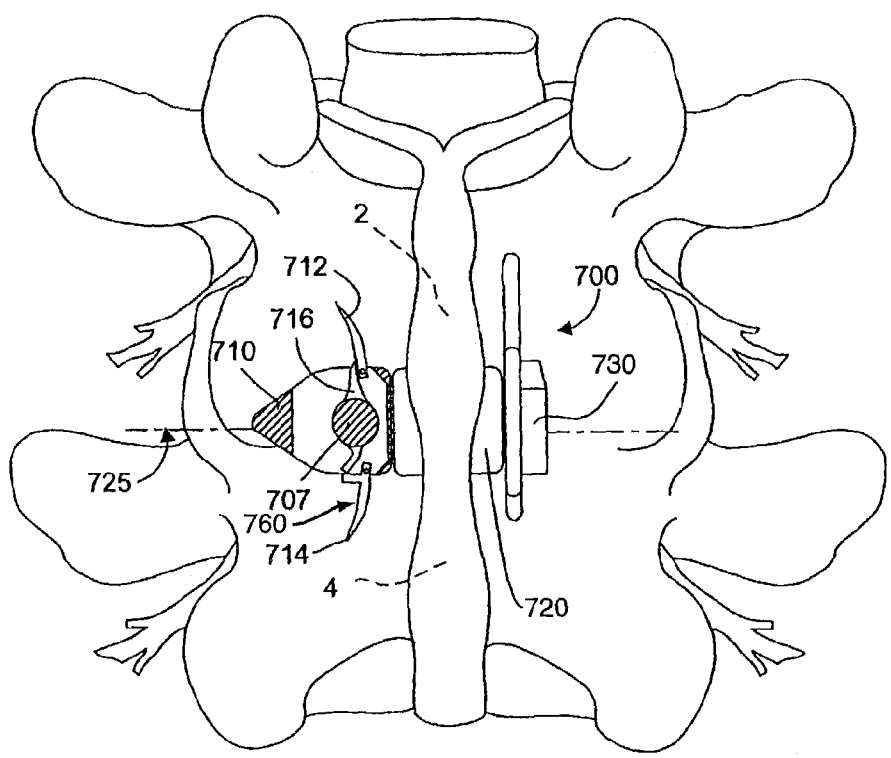
FIG. 9C is a partial cross-sectional side view of the implant of FIG. 9B wherein the winglets deployed.

FIGS. 9A through 9C illustrate a further embodiment of an implant 700 in accordance with the present invention arranged between adjacent spinous processes 2,4. In such an embodiment, upper and lower winglets 712,714 can be disposed within the distraction guide 710 and can be deployed by actuating an actuator arrangement including a shaft connected with a cam 707, the shaft having an engageable head 706, or alternatively including some other mechanism such as a gear. As can be seen in FIG. 9A the implant 700 can be disposed between adjacent spinous processes 2,4 as described above in reference to FIG. 3. The distraction guide 710 of the implant 700 can be employed to pierce and/or distract an interspinous ligament 6 connected between the adjacent spinous process 2,4. The implant 700 can then be urged between the spinous processes 2,4 so that the distraction guide 710 further distracts the interspinous ligament 6 to form a space within which a spacer 720 can be disposed. In the embodiment shown, the spacer 720 can pivot about a central body extending from the first wing 730 of the implant 700. The first wing 730 limits and/or blocks movement along a longitudinal axis 725 of the implant 700 in the direction of insertion.

Once the implant 700 is arranged as desired, the actuator arrangement can be actuated to deploy the upper and lower winglets, 712,714, thereby forming a second wing 760 as shown in FIG. 9C. The second wing 760 limits and/or blocks movement along the longitudinal axis 725 in a direction opposite the direction of insertion. With the second wing 760 deployed, the adjacent spinous processes 2,4 are at least partially disposed between the wings 730,760, preventing the implant 700 from becoming undesirably dislodged from the space between the adjacent spinous processes 2,4. As shown in FIG. 9C, the first wing 730 and the second wing 760 can be arranged sufficiently far apart that the adjacent spinous processes 2,4 can move relative to one another slightly (e.g., laterally—such as during a twisting motion), allowing the patient greater flexibility of movement.

FIGS. 9B and 9C are partial cross-sectional posterior views of the implant 700 shown in FIG. 9A. In an embodiment, the deployable winglets 712,714 can be extended from the distraction guide 710 using an actuator arrangement comprising a shaft 707 and cam 716. The cam 716 can be rotated to force the winglets 712,714 to pivot outward from the distraction guide 710. As shown, the winglets 712,714 are at least partially disposed within a cavity of the distraction guide 710.

Figure 10A:
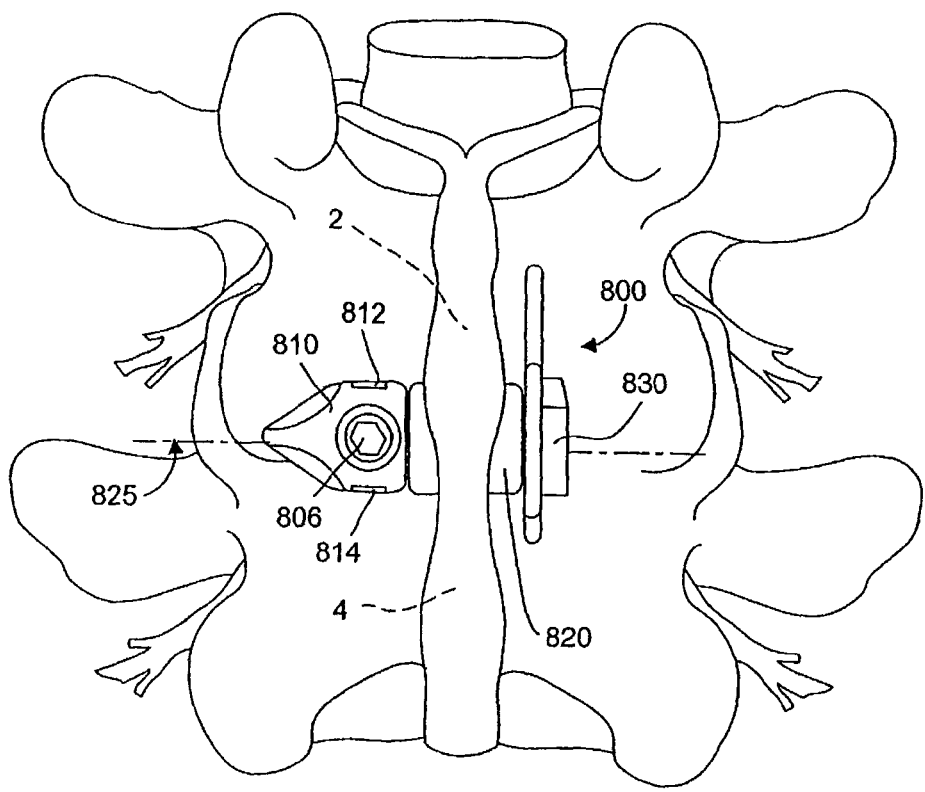
FIG. 10A is a side view of an alternative embodiment of the implant positioned between adjacent spinous processes.

FIGS. 10A through 10E illustrate a still further embodiment of an implant 800 in accordance with the present invention arranged between adjacent spinous processes 2,4. In such an embodiment, upper and lower winglets 812,814 can be disposed within the distraction guide 810 and can be deployed by actuating an actuator arrangement including a screw 807 having an engageable head 806, or alternatively including some other mechanism such as a gear. As can be seen in FIG. 10A the implant 800 can be disposed between adjacent spinous processes 2,4 as described above in reference to FIG. 3. The distraction guide 810 of the implant 800 can be employed to pierce and/or distract an interspinous ligament 6 connected between the adjacent spinous process 2,4. The implant 800 can then be urged between the spinous processes 2,4 so that the distraction guide 810 further distracts the interspinous ligament 6 to form a space within which a spacer 820 can be disposed. In the embodiment shown, the spacer 820 can pivot about a central body extending from the first wing 830 of the implant 800. The first wing 830 limits and/or blocks movement along a longitudinal axis 825 of the implant 800 in the direction of insertion.

Figure 10B:
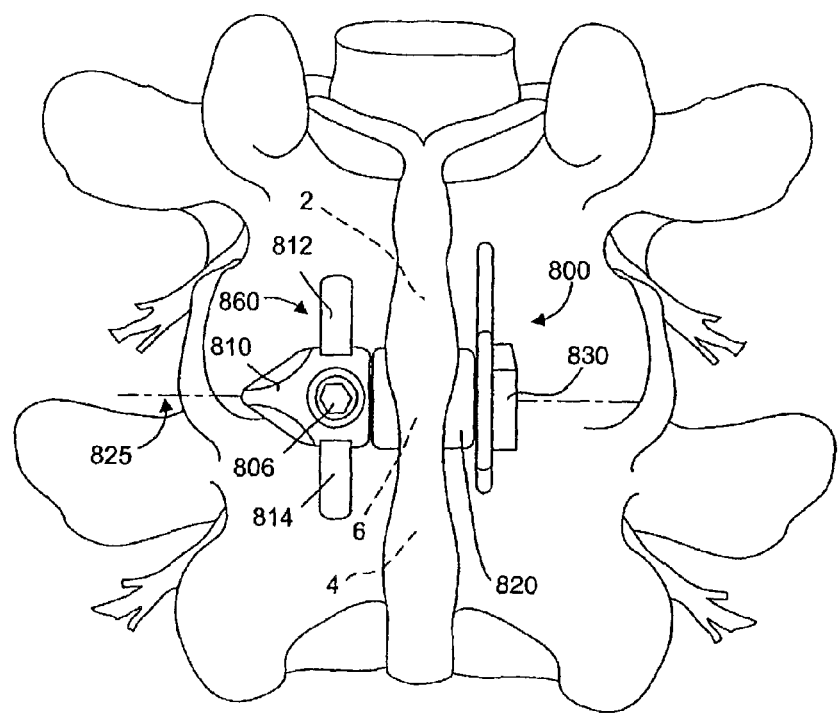
FIG. 10B is a side view of the implant of FIG. 10A positioned between adjacent spinous processes wherein the winglets deployed.

Once the implant 800 is arranged as desired, the actuator arrangement can be actuated to deploy the upper and lower winglets, 812,814, thereby forming a second wing 860 as shown in FIG. 10B. The second wing 860 limits and/or blocks movement along the longitudinal axis 825 in a direction opposite the direction of insertion. With the second wing 860 deployed, the adjacent spinous processes 2,4 are at least partially disposed between the wings 830,860, preventing the implant 800 from becoming undesirably dislodged from the space between the adjacent spinous processes 2,4. As shown in FIG. 9B, the first wing 830 and the second wing 860 can be arranged sufficiently far apart that the adjacent spinous processes 2,4 can move relative to one another slightly (e.g., laterally—such as during a twisting motion), allowing the patient greater flexibility of movement.

Figure 10C:
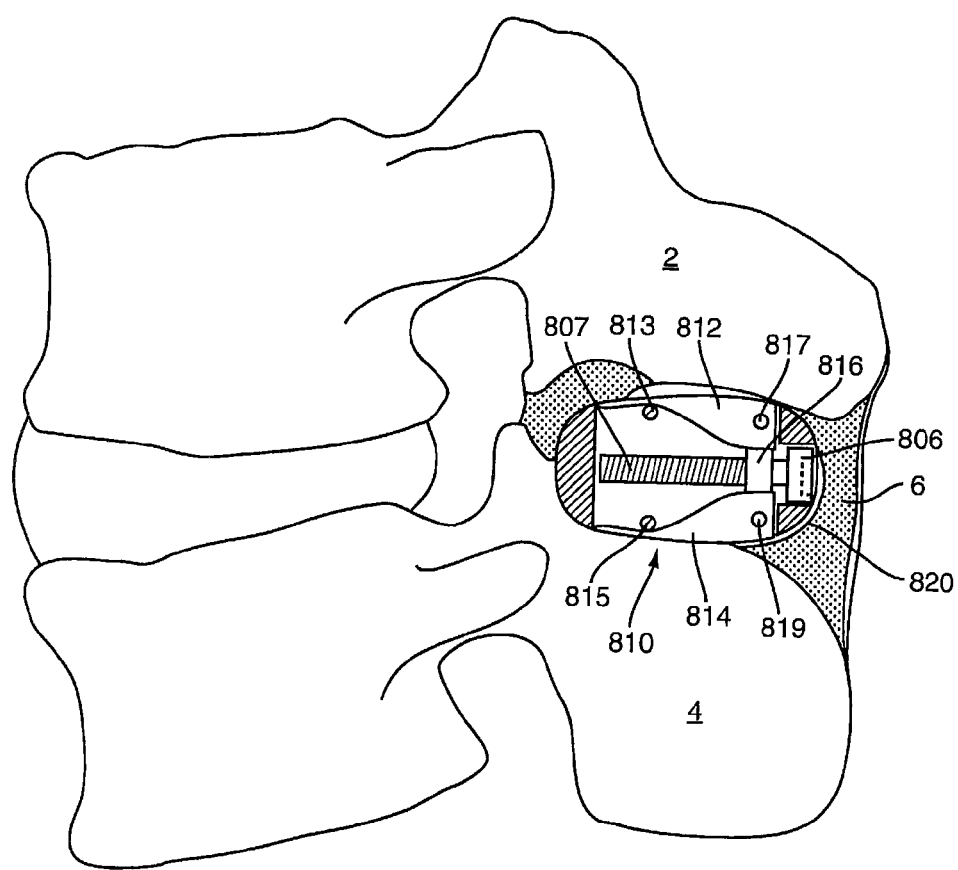
FIG. 10C is a partial cross-sectional end view of the implant of FIG. 10A showing deployable winglets disposed within a distraction guide of the implant.
Figure 10D:
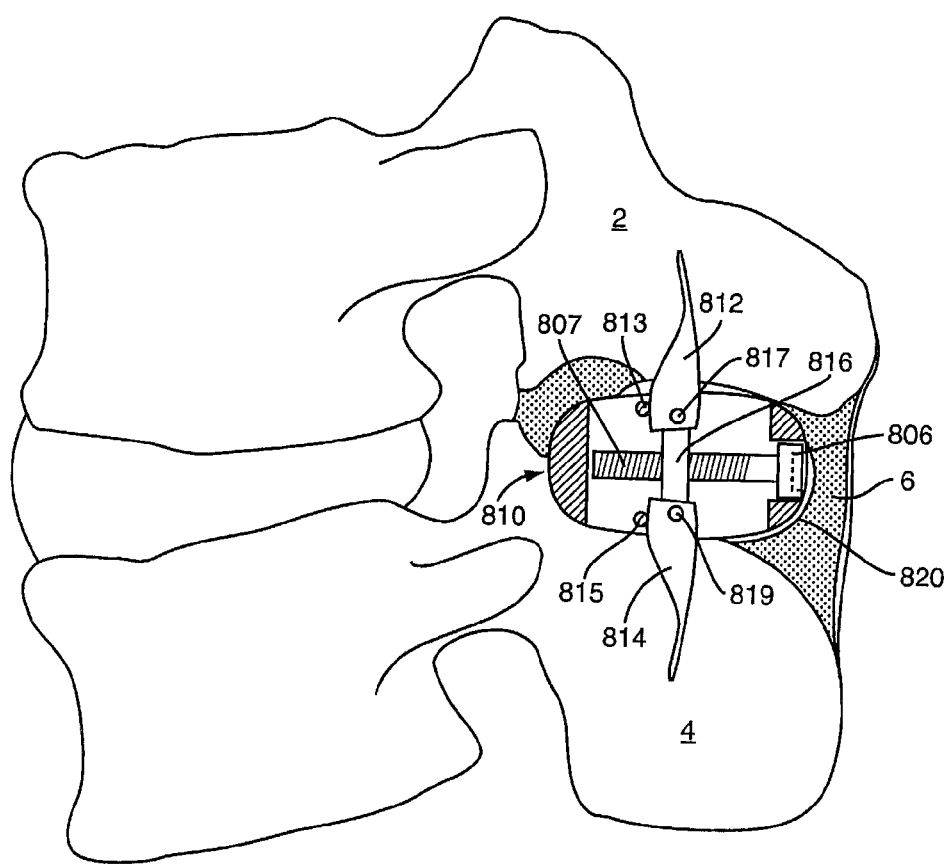
FIG. 10D is a partial cross-sectional end view of the implant of FIGS. 10A-10C showing the winglets deployed so that the winglets extend from the distraction guide of the implant.

FIGS. 10C and 10D are partial cross-sectional end views of the implant 800 shown in FIGS. 10A and 10B. In an embodiment, the deployable winglets 812,814 can be extended from the distraction guide 810 using an actuator arrangement comprising a screw 807 and threaded collar 816. The threaded collar 816 can be driven along the screw 807 to force the winglets 812,814 to pivot outward from the distraction guide 810. As shown, the winglets 812,814 are at least partially disposed within a cavity of the distraction guide 810. The winglets 812,814 are pivotably connected with the threaded collar 816 at an upper pivot point 817 and a lower pivot point 819. Pins 813,815 or other obstruction devices can be disposed within the cavity and arranged so that the pins 813,815 do not interfere with the arrangement of the winglets 812,814 in a nested, or undeployed, position. However, as the threaded collar 816 travels along the screw 807 in a posterior-to-anterior direction, the inner surface of the winglets 812,814 contact the pins 813,815 and the winglets 812,814 pivot away from the distraction guide 810. If desired the winglets 812, 814 can be springbiased against the posts 813,815 such that in the nested positions and in any deployed position the winglets 812,814 are held against the posts 813,815.

Figure 10E:
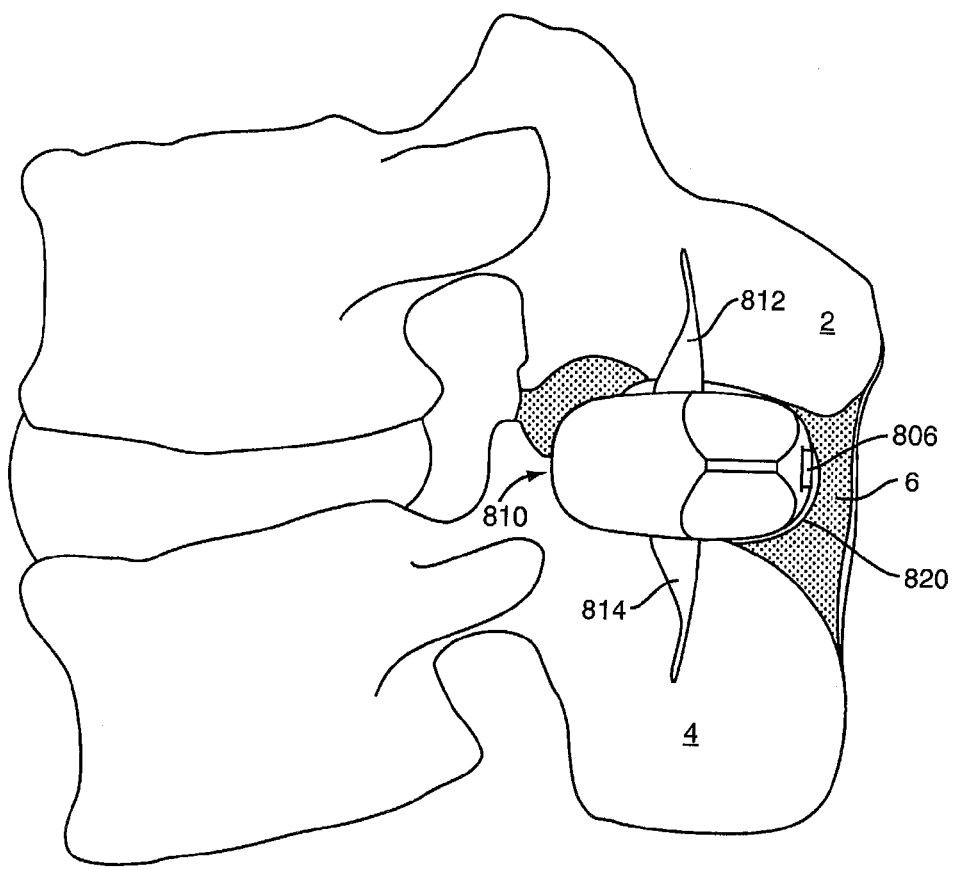
FIG. 10E is an end view of the implant of FIGS. 10A-10D showing the distraction guide and the deployed winglets relative to the distraction guide.

As shown in FIGS. 10D and 10E, when the threaded collar 816 has traveled a distance along the screw 807, the winglets 812,814 are deployed to form a second wing 860. The winglets 812,814 extend along a significant portion of the outer surface of the spinous processes 2,4. When urged along the longitudinal axis 825 in a direction opposite the direction of insertion, the winglets 812,814 contact the adjacent spinous processes 2,4 and resist further movement in said direction. FIG. 10E is an end view of the implant 800 with the second wing 860 deployed. As shown, the screw engageable head 806 extends from the distraction guide 810; however, when implemented, it is preferable for the screw engageable head 806 to be either flush with the surface of the distraction guide 810 or slightly receded from the surface of the distraction guide 810 so that movement of the implant 800 is not obstructed during distraction of the interspinous ligament 6 and/or the spinous processes 2,4. The screw engageable head 806 is shown extending from the distraction guide 810 to demonstrate possible arrangement relative to the proximal end of the distraction guide 810.

Figure 11A:
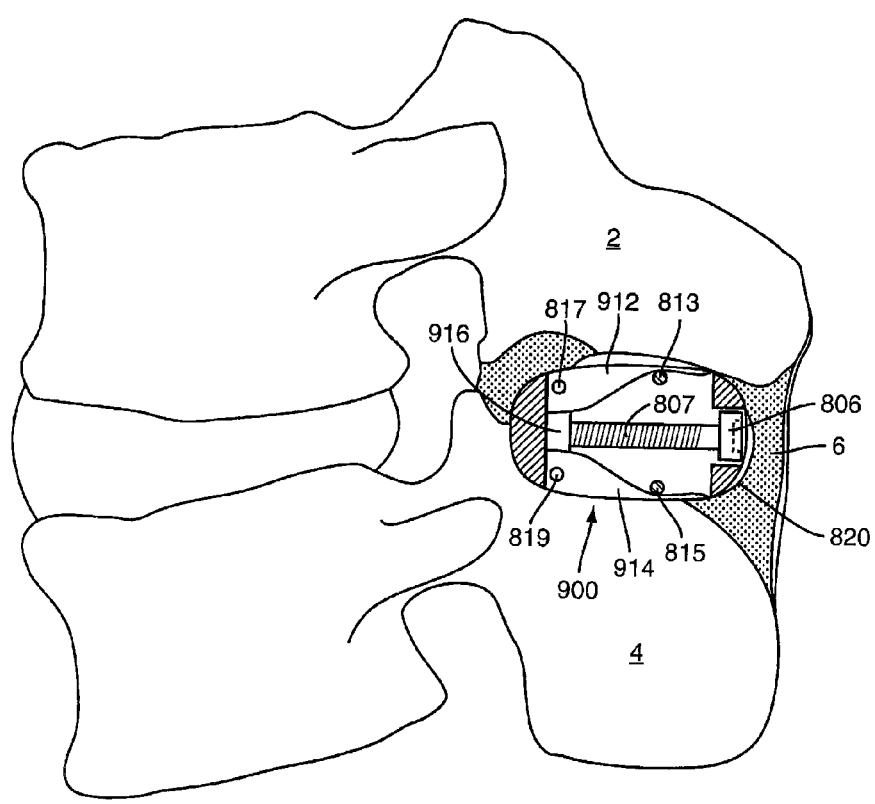
FIG. 11A is a partial cross-sectional end view of an alternative embodiment of an implant in accordance with the present invention including an alternative actuator arrangement.
Figure 11B:
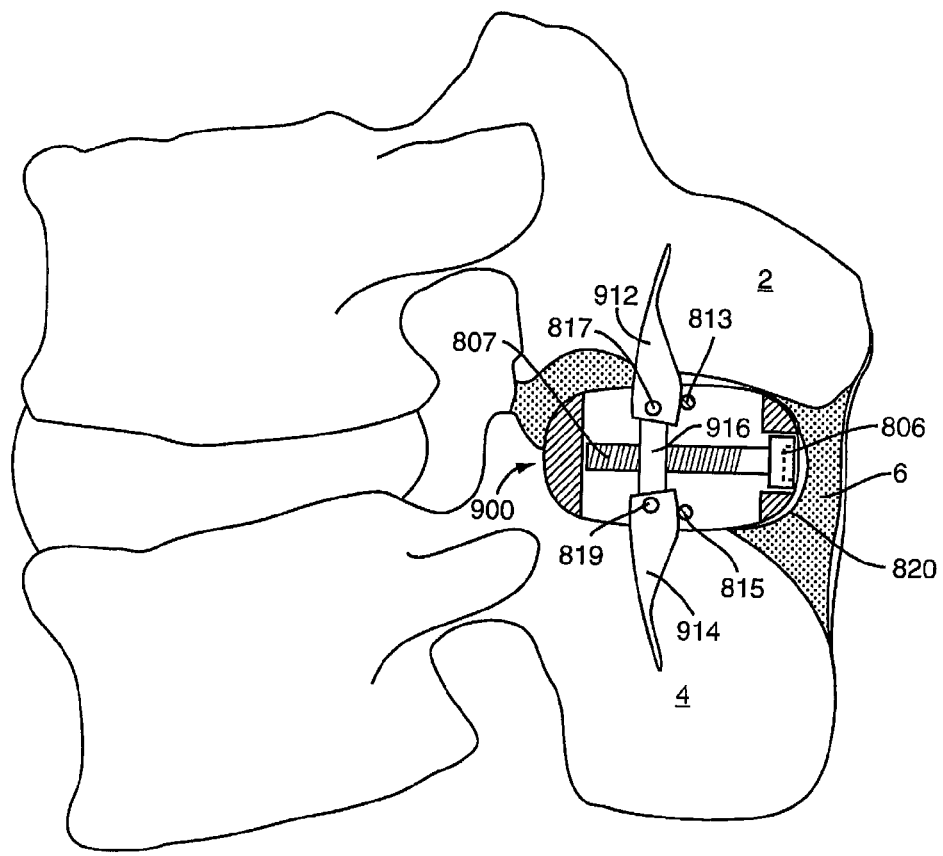
FIG. 11B is an partial cross-sectional end view of the implant of FIG. 11A showing the winglets deployed so that the winglets extend from the distraction guide of the implant.
Figure 12A:
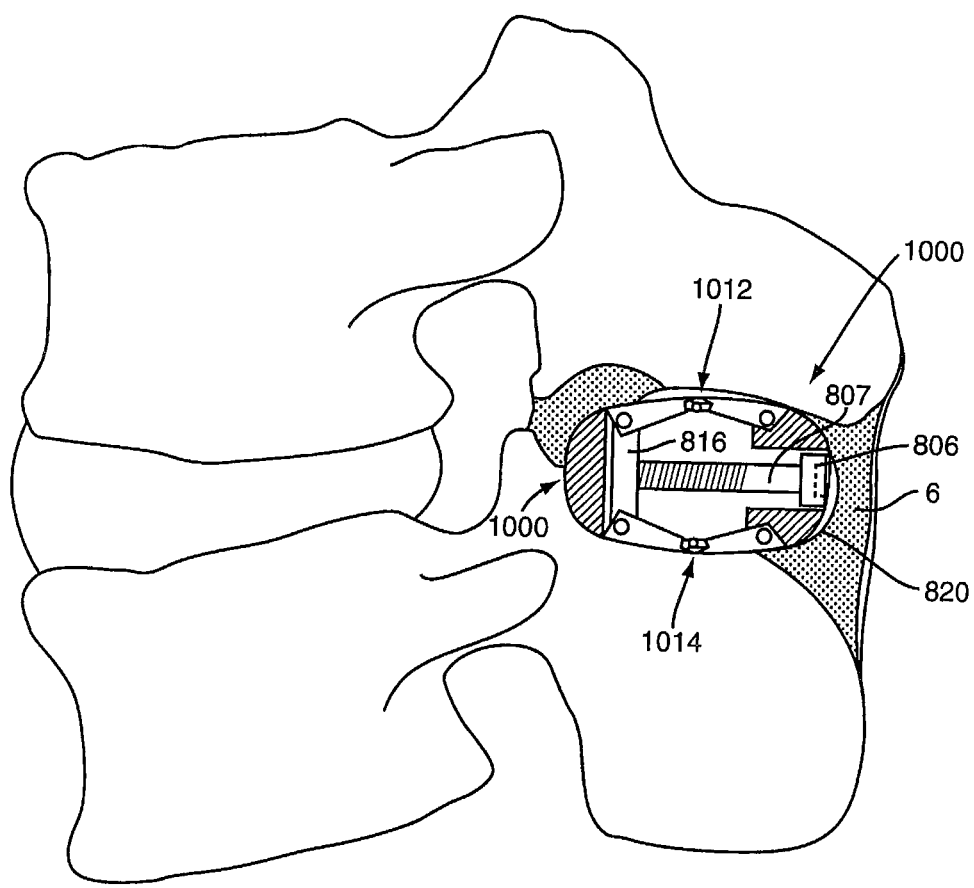
FIG. 12A is a partial cross-sectional end view of still another embodiment of an implant in accordance with the present invention having an alternative actuator arrangement wherein the winglets comprise two hinged portions.
Figure 12B:
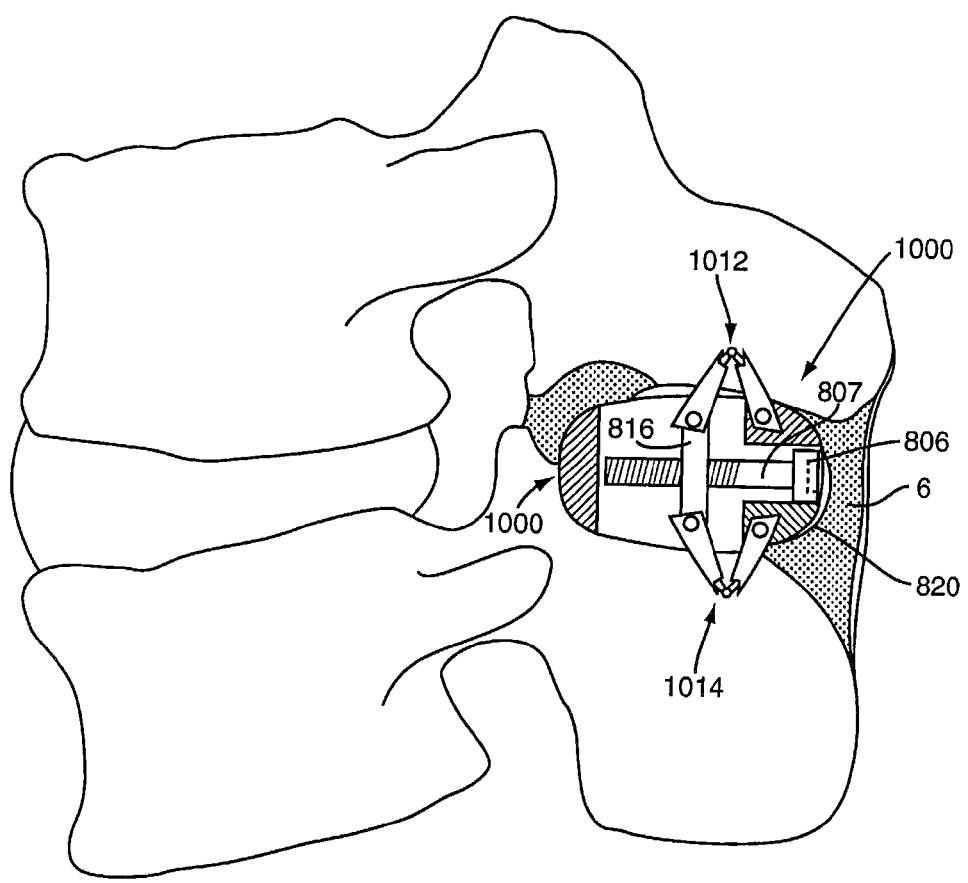
FIG. 12B is a partial cross-sectional end view of the implant of FIG. 12A showing the winglets deployed so that the winglets extend from the distraction guide of the implant.

FIGS. 11A and 11B illustrate yet another embodiment of the implant 900 having an alternative actuation arrangement. In such an embodiment, the winglets 912,914 can be reversed in arrangement so that the winglets 912,914 are deployed by urging the threaded collar 916 toward the screw engageable head 806. FIGS. 12A and 12B illustrate a still further embodiment of the implant 1000 having an alternative actuation arrangement. In such embodiments, the winglets 1012,1014 include two hinged portions, each winglet 1012,1014 folding outward to form a portion of a second wing 1060. The second wing 1060 does not extend as far along the axis of the spine, i.e. the total height of the second wing 1060 along the spine is smaller than previous embodiments. A reduced second wing height can be advantageous where implants are positioned at adjacent motion segments, thereby preventing undesired contact of adjacent implants.

Figure 13:
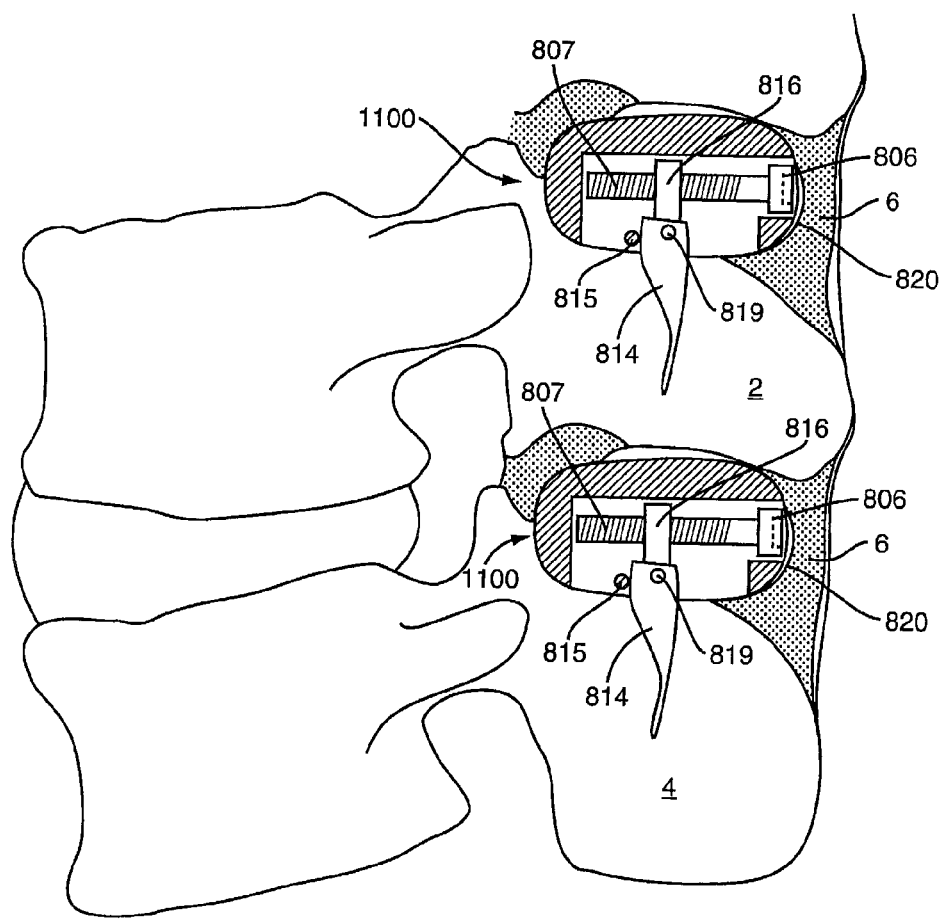
FIG. 13 is a partial cross-sectional end view of a still further embodiment of an implant in accordance with the present invention wherein implants are arranged at adjacent motion segments.

As mentioned above, in other embodiments in accordance with the present invention, the winglets can be deployed from the distraction guide using a mechanism other than a screw and threaded collar. For example, one or more gears can be employed. Further, in still other embodiments the upper and lower winglets can have a shape along other than those shapes shown in FIGS. 10A through 12B. The invention is not intended to be limited to winglets having shapes such as shown. In still further embodiments, such as shown in FIG. 13, the implant 1100 can include only one of the upper and lower winglets. For example, where implants are positioned at adjacent motion segments it can be advantageous to have a lower winglet 814, thereby preventing undesired contact of adjacent implants 1100. As will be obvious to one of ordinary skill in the art, myriad different actuation arrangements can be employed to form a second wing. Implants in accordance with the present invention are not intended to be limited to those described in detail herein.

Materials for Use in Implants of the Present Invention

In some embodiments, the implant, and components of the implant (i.e., the spacer, the distraction guide, etc.) can be fabricated from medical grade metals such as titanium, stainless steel, cobalt chrome, and alloys thereof, or other suitable implant material having similar high strength and biocompatible properties. Additionally, the implant can be at least partially fabricated from a shape memory metal, for example Nitinol, which is a combination of titanium and nickel. Such materials are typically radiopaque, and appear during x-ray imaging, and other types of imaging. Implants in accordance with the present invention, and/or portions thereof can also be fabricated from somewhat flexible and/or deflectable material. In these embodiments, the implant and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. Many polymers, copolymers, blends, and composites of polymers are radiolucent and do not appear during x-ray or other types of imaging. Implants comprising such materials can provide a physician with a less obstructed view of the spine under imaging, than with an implant comprising radiopaque materials entirely. However, the implant need not comprise any radiolucent materials.

One group of biocompatible polymers is the polyaryletherketone group which has several members including polyetheretherketone (PEEK), and polyetherketoneketone (PEKK). PEEK is proven as a durable material for implants, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In an embodiment, the implant can be fabricated from PEEK 450G, which is an unfilled PEEK approved for medical implantation available from Victrex. Other sources of this material include Gharda located in Panoli, India. PEEK 450G has the following approximate properties:

| Property | Value |
|---|---|
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

PEEK 450G has appropriate physical and mechanical properties and is suitable for carrying and spreading a physical load between the adjacent spinous processes. The implant and/or portions thereof can be formed by extrusion, injection, compression molding and/or machining techniques.

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in implants in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the implant can be comprised of polyetherketoneketone (PEKK). Other material that can be used include polyetherketone (PEK), polyetherketoneetherketoneketone (PEKEKK), polyetheretherketoneketone (PEEKK), and generally a polyaryletheretherketone. Further, other polyketones can be used as well as other thermoplastics. Reference to appropriate polymers that can be used in the implant can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, biocompatibility, mechanical strength and abrasion resistance. Other thermoplastic materials and other high molecular weight polymers can be used.

Methods for Implanting Interspinous Implants

Figure 14:
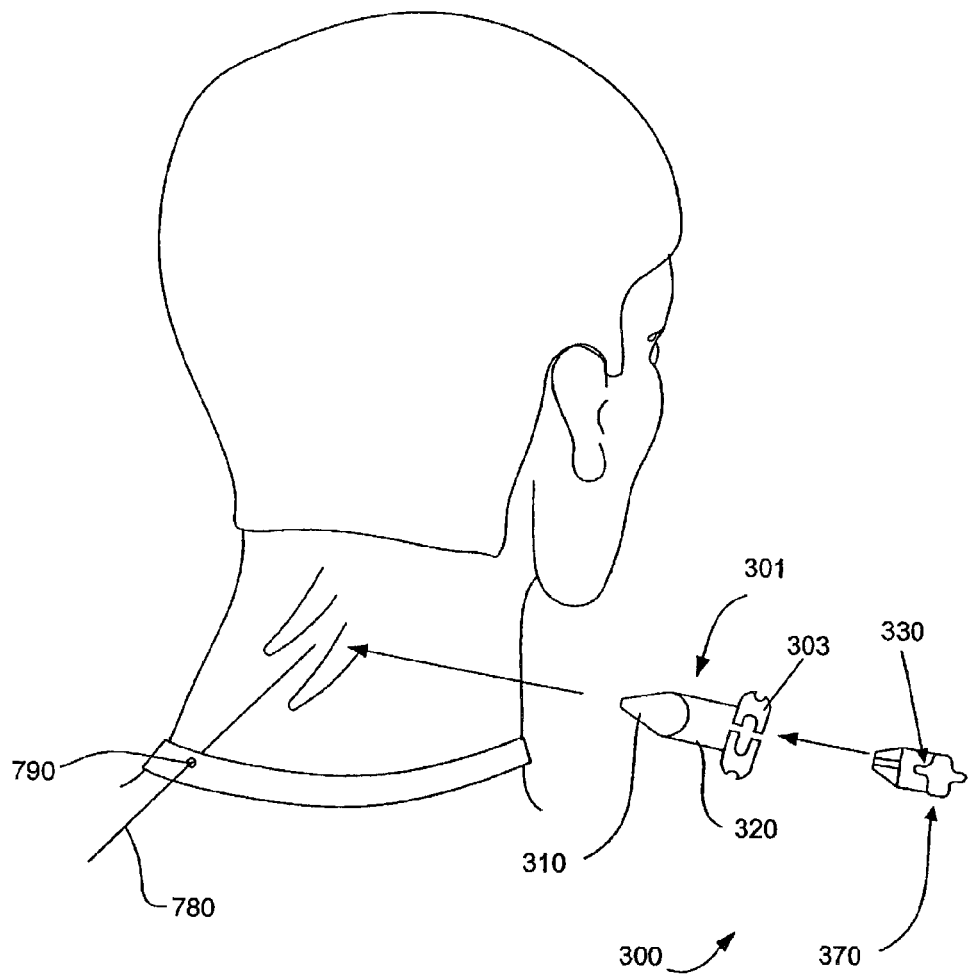
FIG. 14 illustrates an embodiment of a method for implanting the implant of FIGS. 2A-8 between adjacent spinous processes in accordance with the present invention.

A minimally invasive surgical method for implanting an implant 300 as shown in FIGS. 2A-8 in the cervical spine is disclosed and taught herein. In this method, as shown in FIG. 14, preferably a guide wire 780 is inserted through a placement network 790 into the neck of the implant recipient. The guide wire 780 is used to locate where the implant 300 is to be placed relative to the cervical spine, including the spinous processes. Once the guide wire 780 is positioned with the aid of imaging techniques, an incision is made on the side of the neck so that an implant 300 in accordance with an embodiment of the present invention, can be positioned in the neck thorough an incision and along a line that is about perpendicular to the guide wire 780 and directed at the end of the guide wire 780. The main body 301 of the implant 300 is inserted into the neck of the patient. Preferably during insertion, the distraction guide 310 pierces or separates the tissue without severing the tissue.

Once the main body 301 is satisfactorily positioned, an insert 370 can be positioned within a cavity of the main body 301, causing the distraction guide 310 of the main body 301 to be arranged in a second configuration so that at least a portion of the distraction guide 310 forms a second wing. The insert 370 can be inserted along a line that is generally colinear with the line over which the main body 301 is inserted. The anatomy of the neck is such that it is most convenient and minimally invasive to enter the neck from the side with respect to the main body 301 and the insert 370.

Figure 15A:
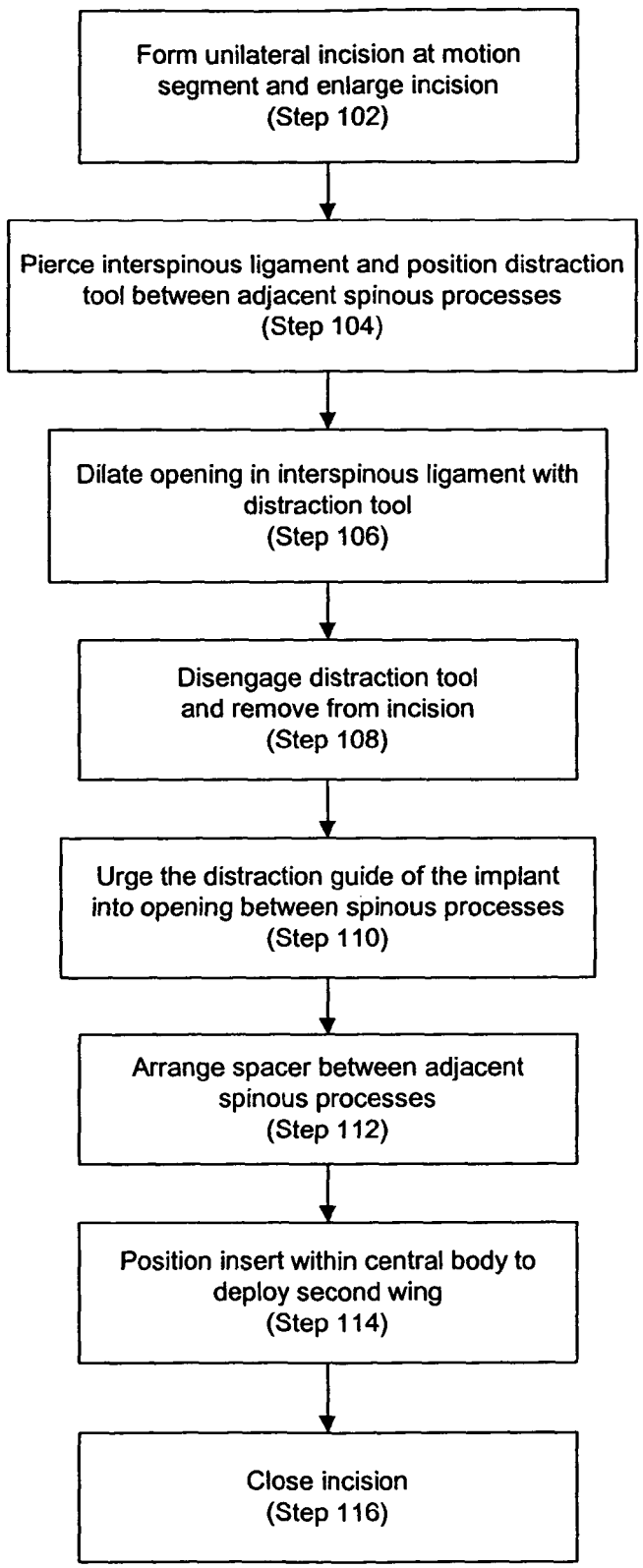
FIG. 15A illustrates an embodiment of a method for implanting the interspinous implant of FIGS. 2A-8 between adjacent spinous processes in accordance with the present invention.

Further, a minimally invasive surgical method for implanting an implant as described in FIGS. 2A-8 in the lumbar spine is disclosed and taught herein. In this method, as shown in the flowchart of FIG. 15A, preferably a unilateral incision or opening can be made using a posterior-anterior approach (Step 102). The unilateral incision can be made, for example, at a location some distance to the left of an axis along the spinous process. The incision or opening can be enlarged, and a distraction tool can be positioned within the incision so that the proximal end of the distraction tool (Step 104) can access an exposed side of the interspinous ligament. The distraction tool can be urged through the interspinous ligament, thereby distracting the interspinous ligament so as to receive the implant (Step 106). Once the interspinous ligament is sufficiently distracted, the distraction tool can be disengaged and removed from the incision (Step 108).

Once the distraction tool has been removed from the incision, the implant can be positioned at the dilated opening, and the distraction guide of the implant can be urged through the dilated opening (Step 110). The implant can be further urged through the opening until the spacer is positioned as desired between the adjacent spinous processes of the targeted motion segment (Step 112). The spacer is free to rotate so that the load is distributed more evenly over the surface of the spinous processes. Optionally, the implant can be urged through the dilated opening until the first wing contacts the adjacent spinous processes, thereby blocking further movement in the direction of insertion. Once the implant is properly arranged, the insert can be positioned at the distal end of the implant so that the insert can be urged into and through the hollow cavity of the hollow central body (Step 114). As the insert is seated inside of the cavity, the distraction guide splits, and the upper winglet and the lower winglet deploy as a second wing. The remaining tools can be removed from the incision, and the incision can be closed (Step 116). Preferably during insertion, the distraction end pieces or separates the tissue without severing the tissue.

Figure 15B:
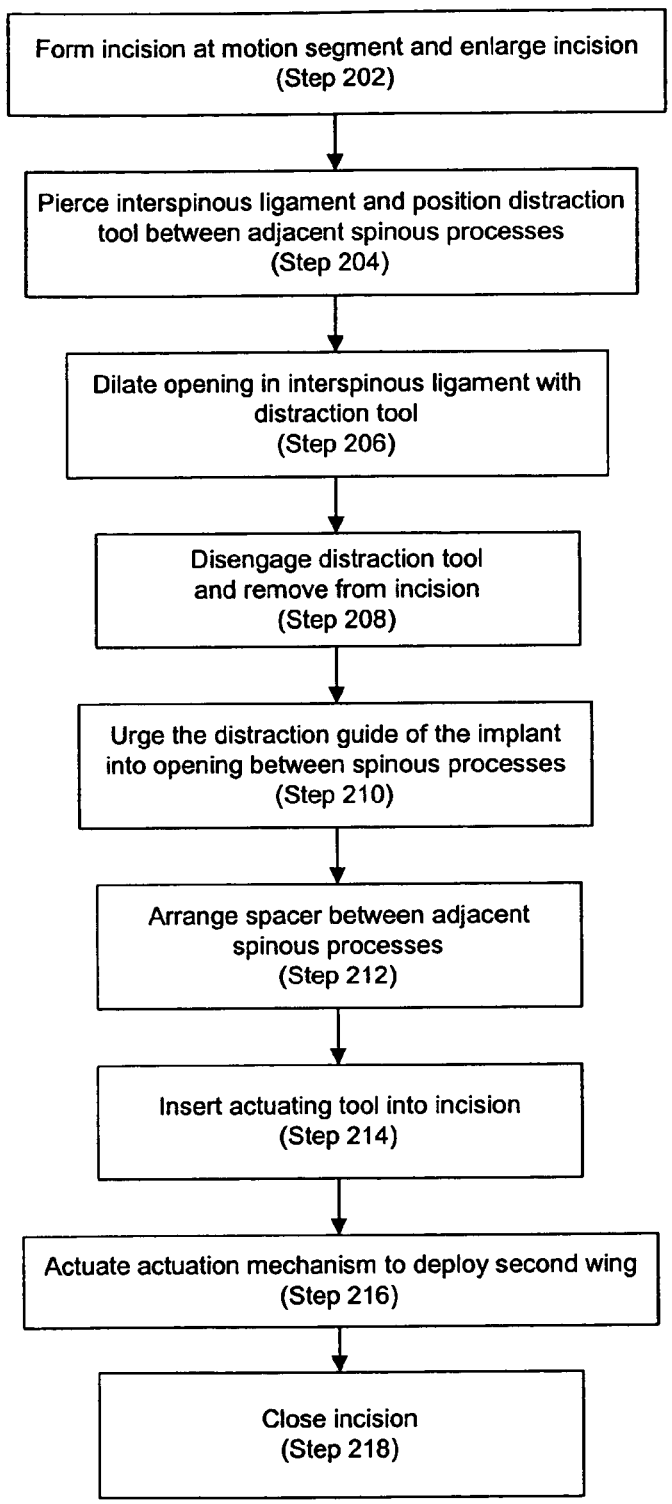
FIG. 15B illustrates an embodiment of a method for implanting the interspinous implant of FIGS. 9A-13 between adjacent spinous processes in accordance with the present invention.

Further, a minimally invasive surgical method for implanting an implant as shown in FIGS. 9A-13 in the lumbar spine is disclosed and taught herein. In this method, as shown in the flowchart of FIG. 15B, an incision or opening can be made using a posterior-anterior approach (Step 202). The incision or opening can be enlarged, and a distraction tool can be positioned within the incision so that the proximal end of the distraction tool (Step 204) can access an exposed side of the interspinous ligament. The distraction guide can be urged through the interspinous ligament and distracted, thereby distracting the interspinous ligament so as to receive the implant (Step 206). Once the interspinous ligament is sufficiently distracted, the distraction tool can be disengaged and removed from the incision (Step 208).

Once the distraction guide has been removed from the incision, the implant can be positioned at the dilated opening, and the distraction guide of the implant can be urged through the dilated opening (Step 210). The implant can be further urged through the opening until the spacer is positioned as desired between the adjacent spinous processes of the targeted motion segment (Step 212). The spacer is free to rotate so that the load is distributed more evenly over the surface of the spinous processes. Optionally, the implant can be urged through the dilated opening until the first wing contacts the adjacent spinous processes, thereby blocking further movement in the direction of insertion. Once the implant is properly arranged, an actuation tool can be inserted within the incision at an opposite side of the adjacent spinous processes from the point of insertion (Step 214). The actuation tool can engage the actuation arrangement, and can actuate the actuation arrangement so that the upper winglet and the lower winglet deploy as a second wing, as described above (Step 216). The remaining tools can be removed from the incision, and the incision can be closed (Step 218). Preferably during insertion, the distraction end pierces or separates the tissue without severing the tissue.

The foregoing description of the present invention have been presented for purposes of illustration and description. It is not intended to be exhaustive or to limit the invention to the precise forms disclosed. Many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed:

1. An interspinous implant adapted to be inserted between spinous processes, the implant comprising:
   a spacer having:
      first and second opposing contact surfaces, each contact surface extending from a most proximal end to a most distal end of the spacer;
      the first and second contact surfaces separated by a first height; wherein the first and second contact surfaces each have a width extending perpendicular to the first height; the width of the contact surfaces being larger than the first height;
      the first and second contact surfaces having no protuberances extending outwardly therefrom;
   a distraction guide disposed on the most distal end of the spacer and comprising first and second wings each being non-flexible and each having a free tip; the distraction guide having first and second configurations;
   each tip being blunt and having a width measured in the same direction as the width of the contact surfaces; the width of the contact surfaces being larger than the width of the tips;
   wherein in the first configuration:
      the tips are disposed closer together such that the first and second wings contact each other proximate their tips;
   wherein in the second configuration:
      the tips are spaced apart from each other;
      the distraction guide limits movement of the interspinous implant when positioned between spinous processes;
   wherein the first and second wings move from the first configuration to the second configuration via rotation about respective rotational axes; the rotational axes of the first and second wings being spaced apart.

2. The implant of claim 1 wherein the implant includes an insert having a third wing; wherein, when the distraction guide is in the second configuration, the spacer is disposed between the third wing and the distraction guide.

3. The implant of claim 1, wherein:
   the spacer includes a cavity; and
   the implant further includes:
      an insert adapted to be urged into the cavity; and
      wherein when the insert is urged into the cavity, the distraction guide is arranged from the first configuration to the second configuration.

4. The implant of claim 3, wherein the insert includes an upper wing portion and a lower wing portion.

5. The implant of claim 1, wherein:
   the first and second wings are pivotably associated with the spacer;
   wherein the distraction guide is arranged in the second configuration by urging the first and second wings to pivot away from each other.

6. The implant of claim 1 wherein each wing has a proximal end disposed proximate the spacer; and wherein in the second configuration the wings extend, from their respective proximal ends to their respective tips, in diverging directions.

7. An interspinous implant adapted to be inserted between spinous processes, the implant comprising:
   a spacer having:
      first and second opposing contact surfaces, each contact surface extending from a most proximal end to a most distal end of the spacer;
      the first and second contact surfaces separated by a first height; wherein the first and second contact surfaces each have a width extending perpendicular to the first height; the width of the contact surfaces being larger than the first height;
      the first and second contact surfaces having no protuberances extending outwardly therefrom;
   a distraction guide disposed on the most distal end of the spacer and comprising first and second wings each being non-flexible and each having a free tip; the distraction guide having first and second configurations;
   each tip being blunt and having a width measured in the same direction as the width of the contact surfaces, the width of the contact surfaces being larger than the width of the tips;
   wherein in the first configuration:
      the tips are disposed closer together such that the first and second wings contact each other proximate their tips;
   wherein in the second configuration:
      the tips are spaced apart from each other;
      the distraction guide limits movement of the interspinous implant when positioned between spinous processes.

8. An interspinous implant adapted to be inserted between spinous processes, the implant comprising:
   a spacer having:
      first and second opposing contact surfaces, each contact surface extending from a most proximal end to a most distal end of the spacer;
      the first and second contact surfaces separated by a first height; wherein the first and second contact surfaces each have a width extending perpendicular to the first height; the width of the contact surfaces being larger than the first height;
      the first and second contact surfaces having no protuberances extending outwardly therefrom;
   a distraction guide disposed on the most distal end of the spacer and comprising first and second wings each being non-flexible; the first wing having a first distal tip and the second wing having a second distal tip;
   the distraction guide having a first insertion configuration and second deployed configuration;
   each tip being blunt and having a width measured in the same direction as the width of the contact surfaces, the width of the contact surfaces being larger than the width of the tips;
   wherein in the first insertion configuration:
      the first and second distal tips define a most distal end of the implant;
      the first and second distal tips are disposed generally parallel to a longitudinal axis;
      the first and second distal tips are disposed closer together than in the second deployed configuration such that the first and second wings contact each other proximate their tips;
   wherein the first wing rotates about a first pivot axis when moving from the insertion configuration to the deployed configuration;

wherein a first distance from the first distal tip of the first wing to the first pivot axis remains constant when the first wing moves from the insertion configuration to the deployed configuration.

9. The implant of claim 8:
wherein the second wing rotates about a second pivot axis when moving from the insertion configuration to the deployed configuration;

wherein a second distance from the second distal tip of the second wing to the second pivot axis remains constant when the second wing moves from the insertion configuration to the deployed configuration.

* * * * *